United States Patent
Shimizu et al.

(10) Patent No.: US 9,069,886 B2
(45) Date of Patent: Jun. 30, 2015

(54) HOME MEDICAL APPARATUS

(75) Inventors: Nobutaka Shimizu, Kanagawa-ken (JP); Suguru Saotome, Hadano (JP); Takumi Shioya, Yokohama (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 33 days.

(21) Appl. No.: 13/240,393

(22) Filed: Sep. 22, 2011

(65) Prior Publication Data

US 2012/0075266 A1 Mar. 29, 2012

(30) Foreign Application Priority Data

Sep. 29, 2010 (JP) ................................. 2010-218496
Sep. 30, 2010 (JP) ................................. 2010-220406

(51) Int. Cl.
*A61M 1/00* (2006.01)
*G06F 3/00* (2006.01)
*G06F 19/00* (2011.01)
(Continued)

(52) U.S. Cl.
CPC ................ *G06F 19/323* (2013.01); *A61M 1/28* (2013.01); *A61M 5/14244* (2013.01); *A61M 2005/14272* (2013.01); *A61M 2205/12* (2013.01); *A61M 2205/502* (2013.01)

(58) Field of Classification Search
CPC ..................... A61M 1/28; A61M 2005/14272; A61M 2205/12; A61M 5/14244; A61M 2005/502; G06F 19/323
USPC .............. 604/29; 715/707; 434/323; 210/646
See application file for complete search history.

(56) References Cited

U.S. PATENT DOCUMENTS

| 5,338,157 A | 8/1994 | Blomquist |
| 6,024,539 A | 2/2000 | Blomquist |

(Continued)

FOREIGN PATENT DOCUMENTS

| CN | 101269247 A | 9/2008 |
| CN | 101360537 A | 2/2009 |

(Continued)

OTHER PUBLICATIONS

Extended European Search Report dated Jan. 31, 2012, issued by the European Patent Office in the corresponding European Application No. 11182447.0. (7 pages).

(Continued)

*Primary Examiner* — Lun-Yi Lao
*Assistant Examiner* — Ibrahim Khan
(74) *Attorney, Agent, or Firm* — Buchanan Ingersoll & Rooney PC

(57) ABSTRACT

A home medical apparatus can give explanations corresponding to the levels of proficiency in operation when explaining to a patient about operation procedures. A home medical apparatus according to this invention includes a selection unit which selects an explanation mode corresponding to the level of proficiency in operation, a storage unit which stores a plurality of display windows classified to the respective explanation modes upon associating them with each other between adjacent levels, and a display control unit which displays the display windows classified to the selected explanation mode in a predetermined order. When a detailed explanation button is pressed, the display control unit makes transition to a display window classified to an explanation mode one level lower than the current explanation mode.

3 Claims, 17 Drawing Sheets

(51) Int. Cl.
*A61M 5/142* (2006.01)
*A61M 1/28* (2006.01)

(56) References Cited

U.S. PATENT DOCUMENTS

| | | | |
|---|---|---|---|
| 6,595,948 B2* | 7/2003 | Suzuki et al. | 604/29 |
| 7,033,539 B2 | 4/2006 | Krensky et al. | |
| 7,410,475 B2 | 8/2008 | Krensky et al. | |
| 2006/0195064 A1 | 8/2006 | Plahey et al. | |
| 2008/0161751 A1 | 7/2008 | Plahey et al. | |
| 2009/0095679 A1* | 4/2009 | Demers et al. | 210/646 |
| 2009/0113335 A1 | 4/2009 | Sandoe et al. | |
| 2009/0222119 A1* | 9/2009 | Plahey et al. | 700/94 |
| 2009/0294339 A1 | 12/2009 | Biewer et al. | |
| 2010/0010428 A1 | 1/2010 | Yu et al. | |
| 2010/0160118 A1 | 6/2010 | Shirasaki et al. | |
| 2010/0292010 A1* | 11/2010 | Kira et al. | 463/43 |
| 2011/0077586 A1 | 3/2011 | Plahey et al. | |

FOREIGN PATENT DOCUMENTS

| | | |
|---|---|---|
| JP | 04-115359 A | 4/1992 |
| JP | 05-083350 A | 4/1993 |
| JP | 08-500515 A | 1/1996 |
| JP | H10-255167 A | 9/1998 |
| JP | 2006-127170 A | 5/2006 |
| JP | 2009-279416 A | 12/2009 |
| JP | 2010-050596 A | 3/2010 |
| JP | 2010-188164 A | 9/2010 |
| WO | WO 03/099355 A2 | 12/2003 |
| WO | WO 2007/072116 A1 | 6/2007 |
| WO | WO 2009/081241 A1 | 7/2009 |

OTHER PUBLICATIONS

Office Action (Final Rejection) issued Nov. 25, 2014 by the Japanese Patent Office in corresponding Japanse Patent Application No. 2010-218496.

Office Action issued Feb. 10, 2015, by the Chinese Patent Office in corresponding Chinese Patent Application No. 201110302684.7.

* cited by examiner

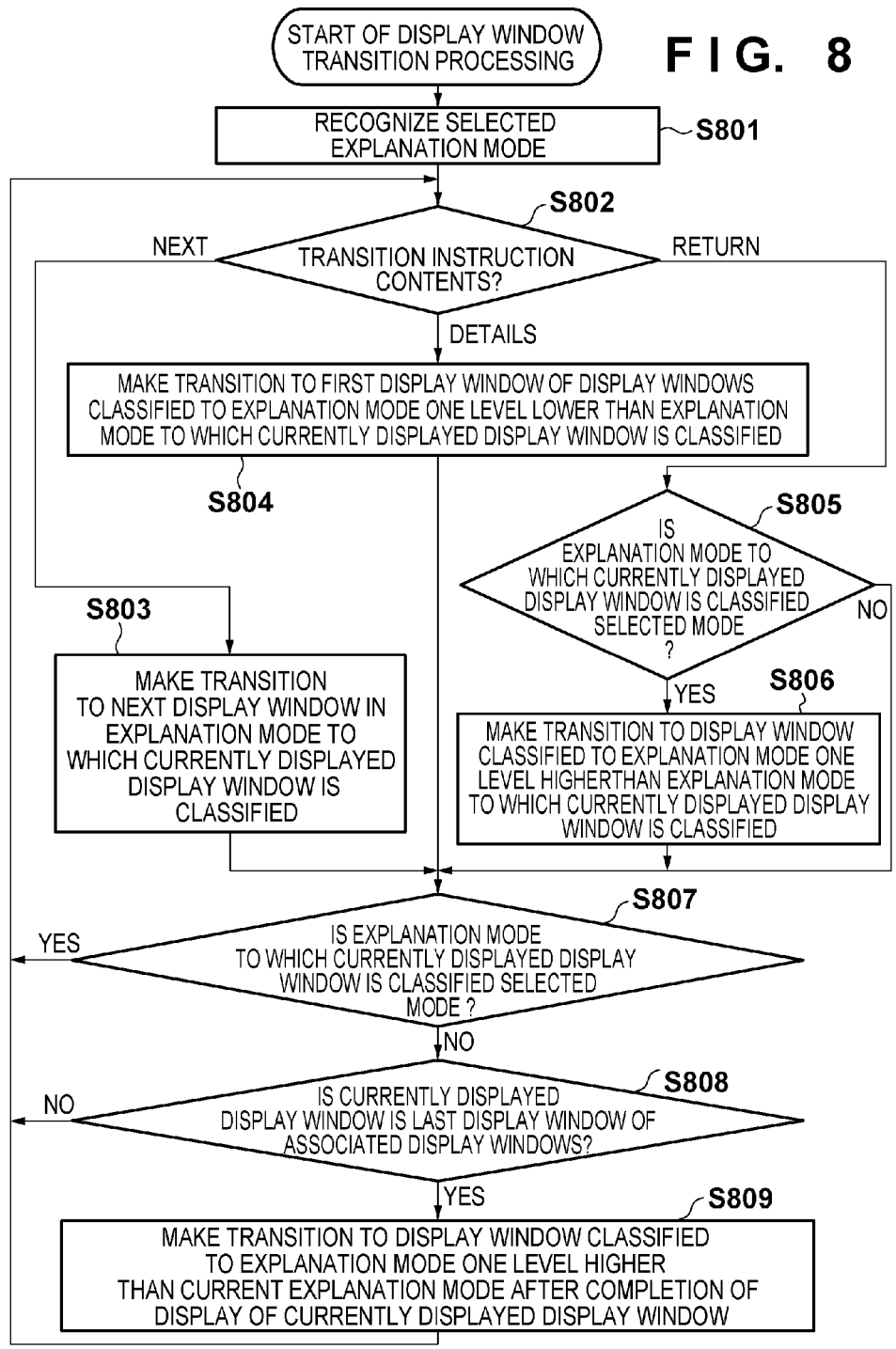

FIG. 9B
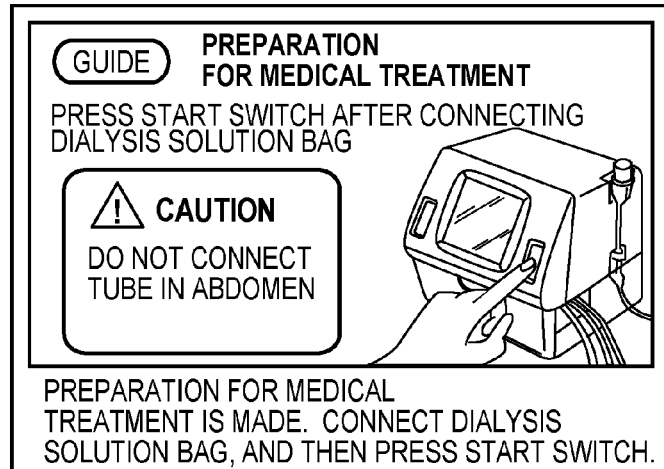
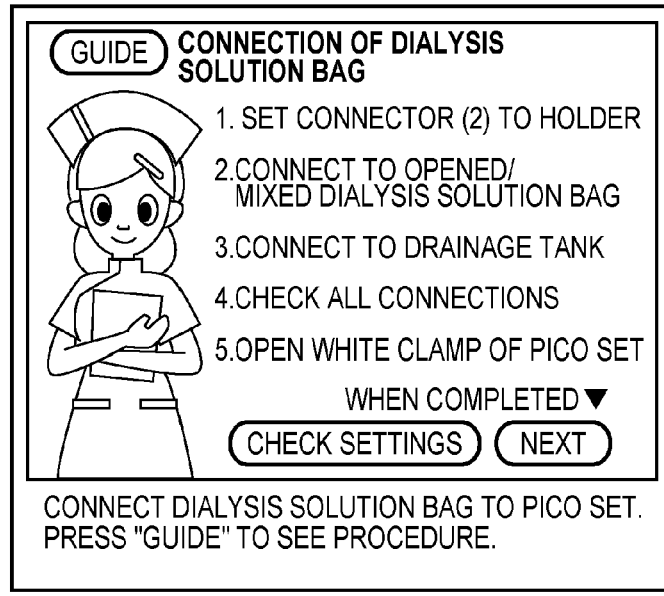
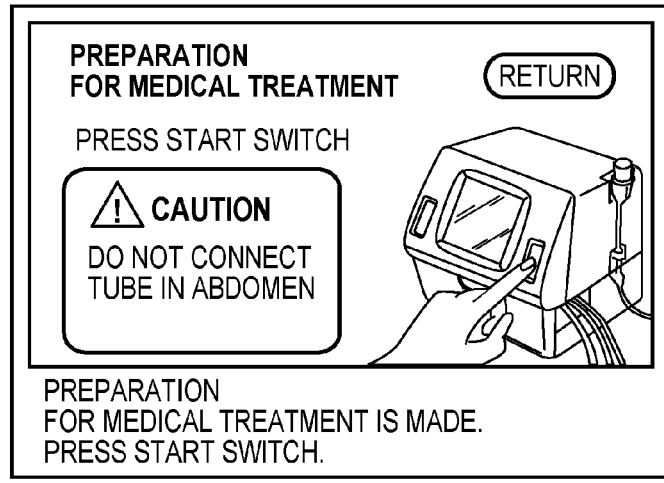

FIG. 9C
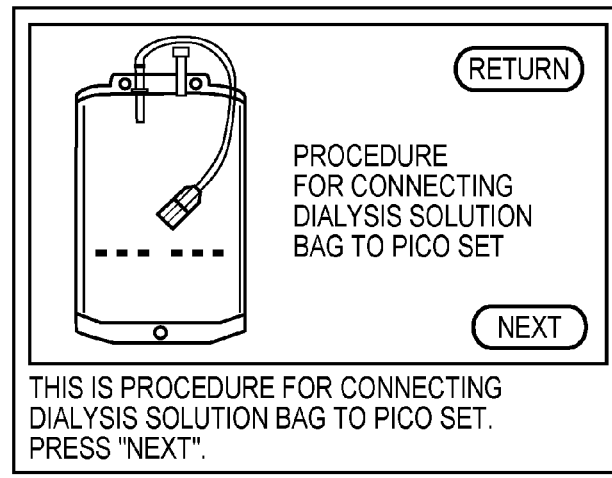
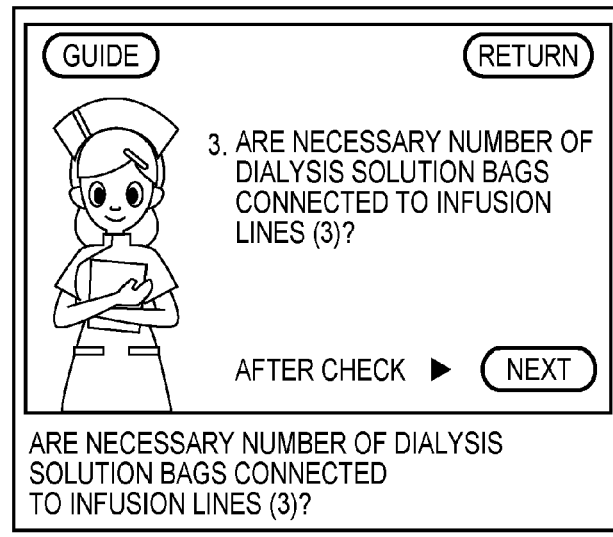
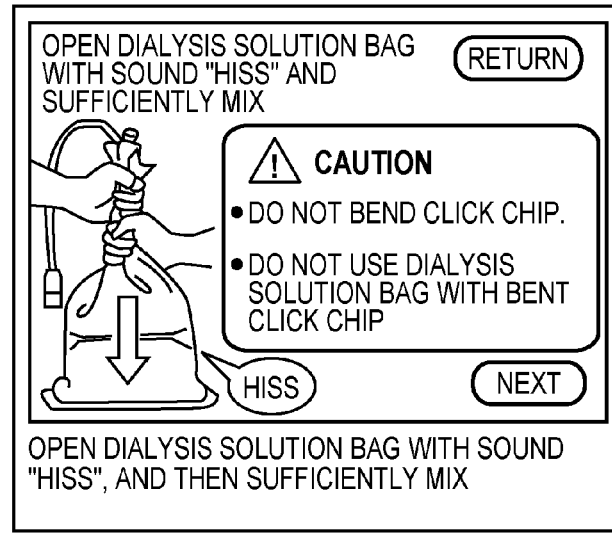

FIG. 9D
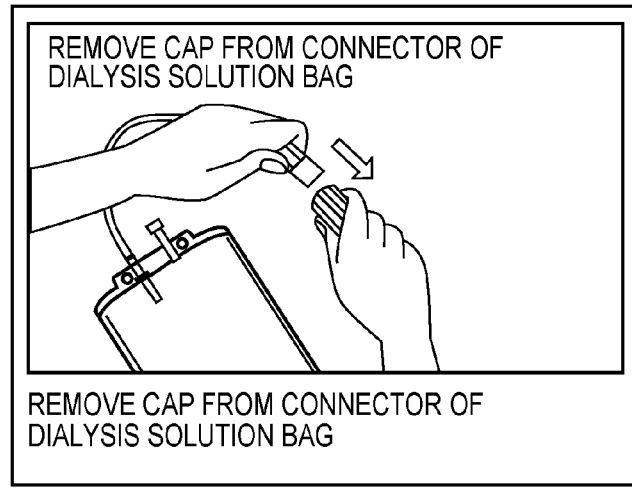
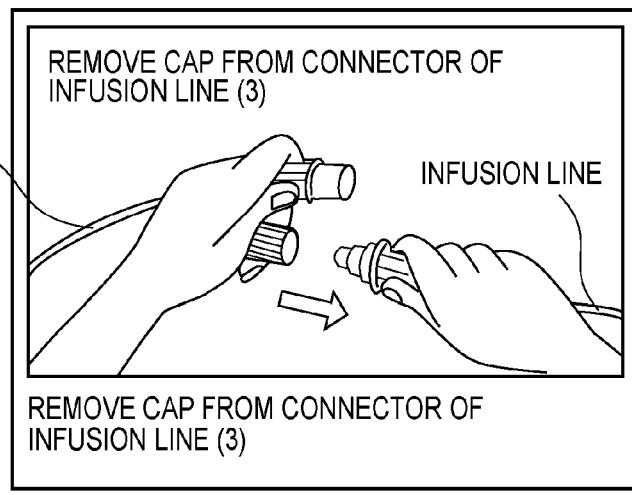
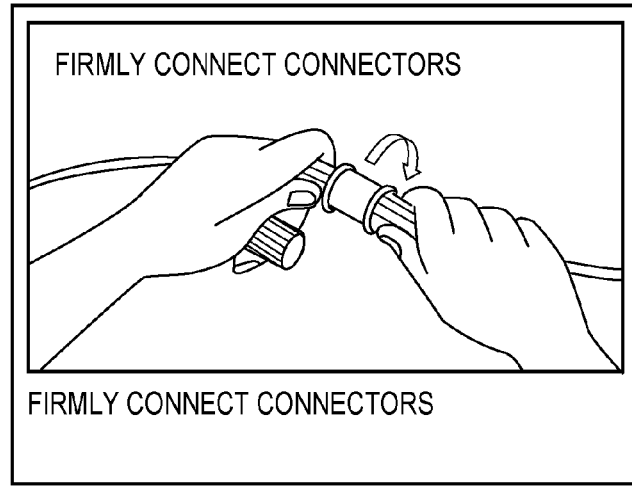

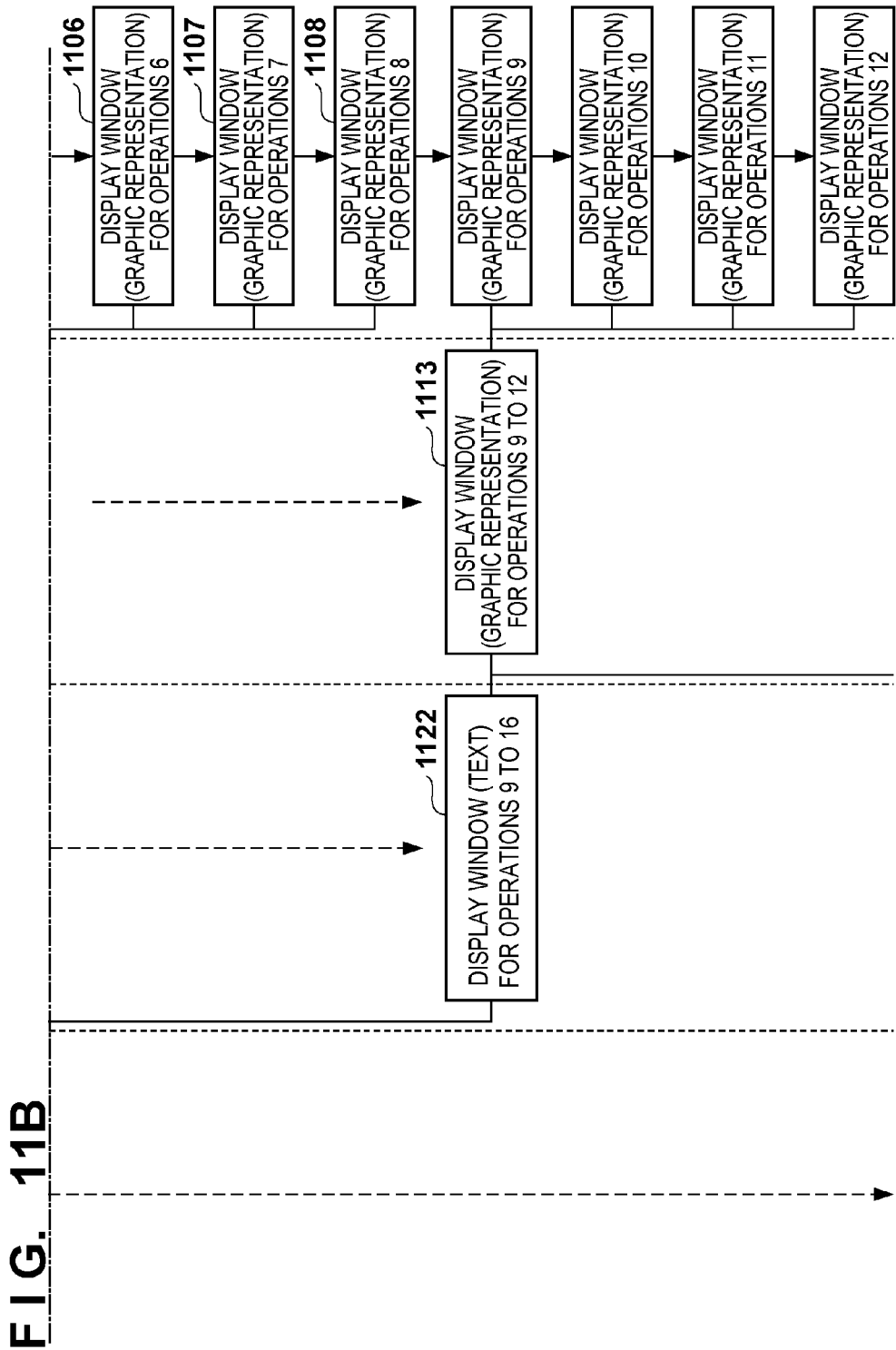

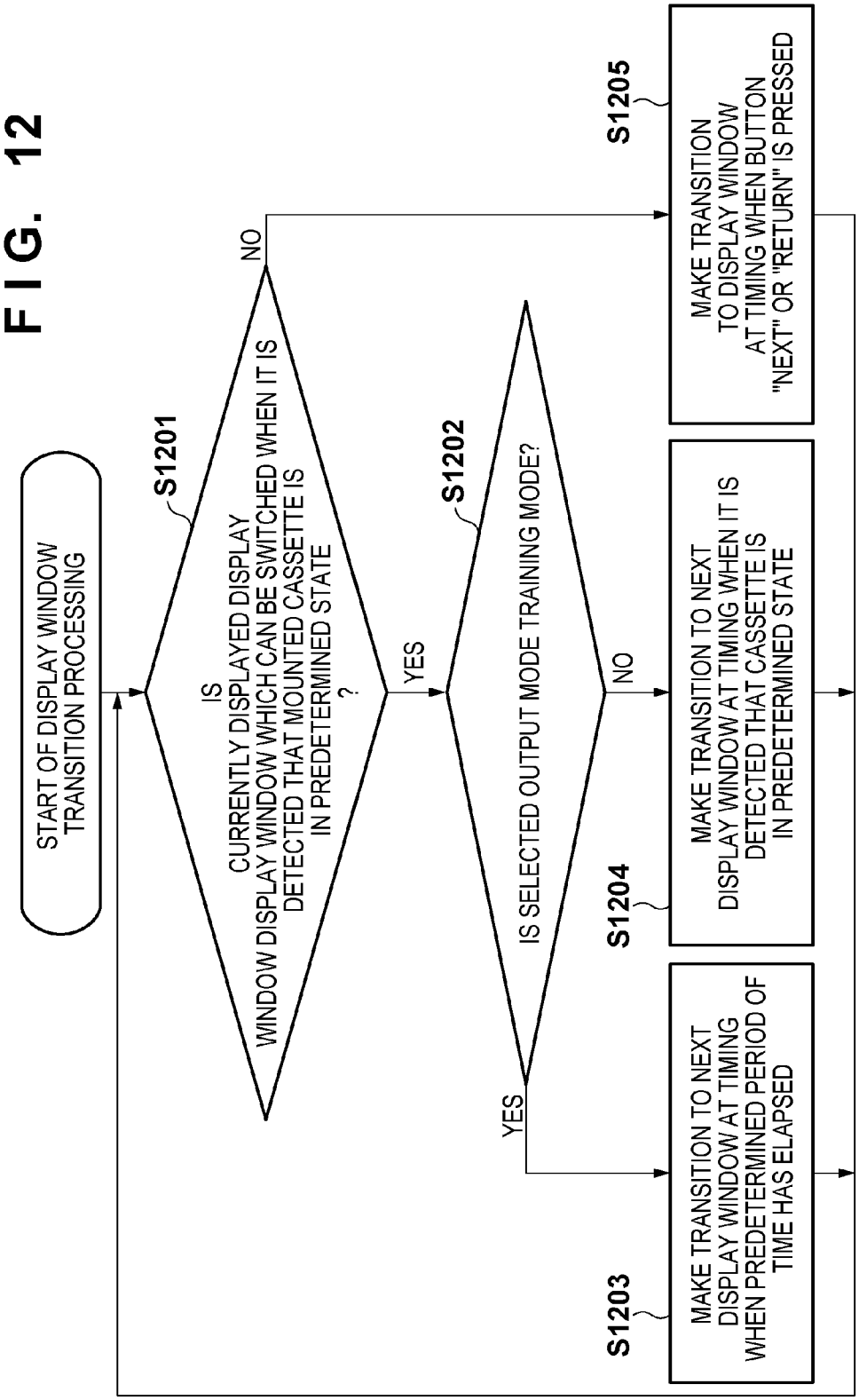

HOME MEDICAL APPARATUS

BACKGROUND OF THE INVENTION

1. Field of the Invention

The present invention relates to a home medical apparatus and, more particularly, to a peritoneal dialysis apparatus.

2. Description of the Related Art

An oxygen enricher configured to allow oxygen inhalation, a peritoneal dialysis apparatus configured to allow peritoneal dialysis, and the like have been widely used as home medical apparatuses for allowing patients themselves to perform medical treatment in their homes and the like.

Of these apparatuses, the peritoneal dialysis apparatus is configured to connect, to a cassette, a catheter tube (dialysis catheter) to be indwelled in the peritoneal cavity of a patient, a dialysis solution bag containing a dialysis solution, and a drainage bag to recover the drainage of dialysis solution, according to a predetermined operation procedure. This cassette is then set in the peritoneal dialysis apparatus. Operating the peritoneal dialysis apparatus allows a dialysis solution to be automatically injected and recover the drainage of dialysis solution at any time during the day or night.

When operating the peritoneal dialysis apparatus, therefore, it is important for a patient to accurately proceed with the operation in accordance with a predetermined operation procedure. A conventional peritoneal dialysis apparatus includes a function of displaying a detailed explanation of an operation procedure by using graphic representation, a function of outputting an explanation by using a voice guide, or the like (see, for example, Japanese Patent Laid-Open No. 2009-279416).

Some patients are familiar with performing peritoneal dialysis by using peritoneal dialysis apparatuses. If a peritoneal dialysis apparatus is configured to explain operation procedures as precise as that for patients who are unfamiliar with operation procedures, such an arrangement will lead to inconvenience to patients who are familiar with the operation procedure.

On the other hand, even a patient familiar with the operation procedure may need to receive a detail explanation of an operation procedure for some specific operation. For this reason, under the premise that explanations of operation procedures should be made to eliminate operation mistakes, a peritoneal dialysis apparatus is preferably configured to provide explanations in accordance with patients at various levels of proficiency in operation procedures, ranging from patients who are unfamiliar with the operation procedures to patients who are familiar with them.

In addition, a doctor or the like generally explains, in advance, to a patient who is to use the above peritoneal dialysis apparatus for the first time how to perform peritoneal dialysis by using the peritoneal dialysis apparatus. The peritoneal dialysis apparatus therefore preferably includes a training function to allow a doctor or the like to give a patient an easily comprehensible explanation of a method of handling the apparatus and the like as well as the above explanation function of allowing the patient to accurately proceed with the operation by himself/herself.

Some conventional peritoneal dialysis apparatuses are configured, from the viewpoint of ensuring safety for a patient who performs peritoneal dialysis, to permit some display window displayed by the explanation function to switch to a display window displaying the next operation procedure only when the mounted cassette satisfies a predetermined condition.

For this reason, when a doctor or the like wants to give a patient only an explanation of how to perform peritoneal dialysis without actually performing peritoneal dialysis, he/she inevitably explains the patient while skipping some of display windows to be displayed. This makes it difficult to give a sufficient explanation and leads to a lack of sense of realism.

SUMMARY OF THE INVENTION

The present invention has been made in consideration of the above problems.

A home medical apparatus according to the present invention has the following arrangement. That is, a home medical apparatus configured to display an operation procedure on a display unit, comprising: a selection unit configured to select one of a plurality of explanation modes having different contents of explanations associated with the operation procedure in accordance with levels of proficiency in the operation procedure; a storage unit configured to store a plurality of display windows displaying explanations associated with the operation procedure upon classifying the display windows to explanation modes corresponding to the levels of proficiency in the operation procedure in accordance with contents of the respective explanations, and storing display windows, of the plurality of display windows classified to the respective explanation modes, which are classified to explanation modes of adjacent levels when the explanation modes are hierarchically ranked in accordance with the levels of proficiency in the operation procedure, upon associating the display windows with each other in accordance with an operation purpose; and a display control unit configured to display display-windows classified to an explanation mode selected by the selection unit on the display unit in a predetermined order.

According to the present invention, a home medical apparatus, specifically a peritoneal dialysis apparatus, can explain operation procedures to a patient in accordance with his/her level of proficiency in operation procedures when explaining to the patient about the operation procedures.

The other present invention has been made in consideration of the above problems.

A home medical apparatus according to the present invention has the following arrangement. That is, a home medical apparatus configured to display operation procedures on a display unit, comprising: a storage unit configured to store display windows respectively displaying the operation procedures; a display control unit configured to control switching of display of the display windows so as to display the display windows on the display unit in a predetermined order; and a selection unit configured to select one of a normal mode and a training mode with different methods of switching display of the display windows.

According to the present invention, the home medical apparatus can explain operation procedures for an actual medical treatment to a patient even when performing no actual medical treatment based on a prescription.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 8 is a flowchart showing a procedure for display window transition processing for controlling the transition of display windows;

FIGS. 9A to 9D are views showing an example of the transition of display windows in the respective explanation modes;

FIGS. 11A and 11B are views showing the transition of display windows in the respective explanation mode and the respective output modes; and FIG. 12 is a flowchart showing a procedure for display window transition processing in the display unit.

DESCRIPTION OF THE EMBODIMENTS

Embodiments of the present invention will now be described in detail in accordance with the accompanying drawings.

Each embodiment of the present invention is described below with reference to the accompanying drawings. Although a peritoneal dialysis apparatus is described as a medical apparatus at home (home medical apparatus), the home medical apparatus of the present invention is not limited to a peritoneal dialysis apparatus. For example, the present invention can be applied to other types of home medical apparatuses such as an oxygen concentrator and a medical infusion apparatus.

First Embodiment

1. Outer Arrangement of Peritoneal Dialysis Apparatus

Figure 1:
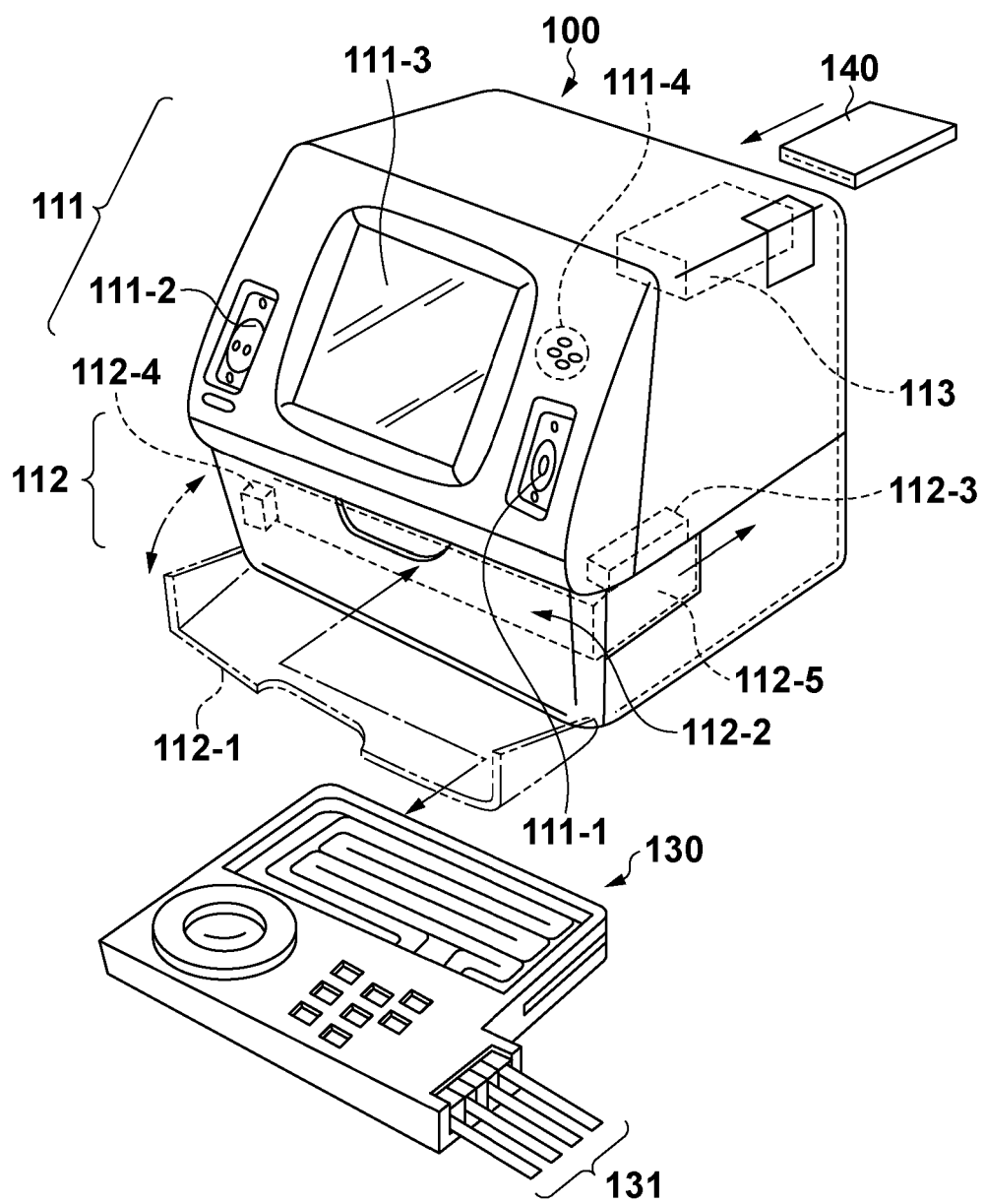
FIG. 1 is a perspective view showing the outer arrangement of a peritoneal dialysis apparatus 100 according to an embodiment of the present invention.

The outer arrangement of the peritoneal dialysis apparatus is described first. FIG. 1 is a perspective view showing the outer arrangement of a peritoneal dialysis apparatus 100 according to an embodiment of the present invention.

As shown in FIG. 1, the peritoneal dialysis apparatus 100 is configured to make a cassette 130 as an accessory and a card 140 detachable. The cassette 130 is configured such that a dialysis solution bag, a drainage tank, a transfer tube set, and the like are connected to the cassette through a connection unit 131. The dialysis solution bag contains a dialysis solution to be injected (infused) into the peritoneum (peritoneal cavity) of a patient. The drainage tank recovers the drainage discharged from the peritoneal cavity of the patient. A dialysis catheter for infusing a dialysis solution is connected to the transfer tube set. The cassette 130 is mounted in the peritoneal dialysis apparatus 100. The peritoneal dialysis apparatus 100 is controlled to inject a dialysis solution into the patient and discharge a dialysis solution from the patient. The card 140 records information about a patient (for example, a patient ID, past dialysis prescription, current dialysis prescription, renal function values: residual renal Kt/V and PD·Kt/V (Kt/V based on peritoneal dialysis), Cr·D/P based on PET test (ratio between creatinine concentration P in serum and creatinine concentration D in peritoneal dialysis drainage), peritoneal function value, and the like). Mounting the card 140 in the peritoneal dialysis apparatus 100 allows the apparatus to recognize the information about the patient who performs peritoneal dialysis.

The detailed arrangement of the cassette 130 is described later. The peritoneal dialysis apparatus 100 is described in detail below.

The peritoneal dialysis apparatus 100 includes a user interface unit 111 and a cassette mounting portion 112 on the front surface side, and includes a card mounting portion 113 in which the card 140 is mounted on the rear surface side.

The user interface unit 111 further includes a start instruction unit 111-1 which issues an instruction to start peritoneal dialysis, a stop instruction unit 111-2 which issues an instruction to stop peritoneal dialysis, a display unit 111-3 which includes a touch panel having a liquid crystal (LCD) panel or organic EL panel, and an audio speaker 111-4 which outputs voice. In this arrangement, when the patient presses the start instruction unit 111-1 while the power supply is ON, the display unit 111-3 displays an operation procedure for performing peritoneal dialysis, and the audio speaker 111-4 outputs voice guidance. This allows the patient to proceed with various operations for peritoneal dialysis in accordance with the operation procedure displayed by the display unit 111-3, which performs color liquid crystal display or organic EL display, and the voice guidance output from the audio speaker 111-4 while sequentially operating the touch panel of the display unit 111-3.

The cassette mounting portion 112 includes a lid member 112-1 which is pivotally mounted on the housing of the peritoneal dialysis apparatus 100. The lid member 112-1 is provided with a closed state sensor 112-4 at a closed position, which detects the closed state of the lid member 112-1.

At the closed position, the lid member 112-1 completely covers an opening portion 112-2 in which the cassette 130 is inserted. The opening portion 112-2 exposed at the open position of the lid member 112-1 incorporates a bubble sensor 112-3 which detects the presence/absence of bubbles contained in a dialysis solution supplied into the cassette 130 mounted in the cassette mounting portion 112.

A shielding plate 112-5 is provided on a side surface of the housing of the peritoneal dialysis apparatus 100 so as to be movable in the direction indicated by the arrow. The shielding plate 112-5 is configured such that when the cassette 130 is mounted in the cassette mounting portion 112, the dialysis solution bag, drainage bag, transfer tube set, and the like to which a dialysis catheter is connected, which are connected to the cassette 130 through the connection unit 131 do not interfere with the side surface of the housing of the peritoneal dialysis apparatus 100.

The card mounting portion 113 is provided with an opening portion (not shown) in which the card 140 is inserted. The opening portion incorporates a card reader which reads the information about the patient (including peritoneal function values: residual renal Kt/V and PD·Kt/V (Kt/V based on peritoneal dialysis), Cr·D/P based on PET test (ratio between creatinine concentration P in serum and creatinine concentration D in peritoneal dialysis drainage)) and medical treatment information of the patient which are recorded on the card 140 mounted in the card mounting portion 113.

2. Flow Path Arrangement for Injection/Discharge of Dialysis Solution

A flow path arrangement for injection and discharge of a dialysis solution into and from the patient is described next. As indicated by 2a and 2b in FIG. 2, a dialysis solution bag 201 is connected to a connecting portion 211 of the connection unit 131 of the cassette 130 through an infusion tube. An additional dialysis solution bag 202 containing a dialysis solution having a concentration different from that of the dialysis solution contained in the dialysis solution bag 201 is connected to a connecting portion 212 through an additional infusion tube. In addition, a drainage tank 203 is connected to a connecting portion 213 through a drainage tube. A transfer tube set 204 whose one end is connected to a dialysis catheter is connected to a connecting portion 214 through an infusion/drainage tube. Note that part of a dialysis catheter 205 is dwelled in the peritoneal cavity of the patient.

Figure 2:
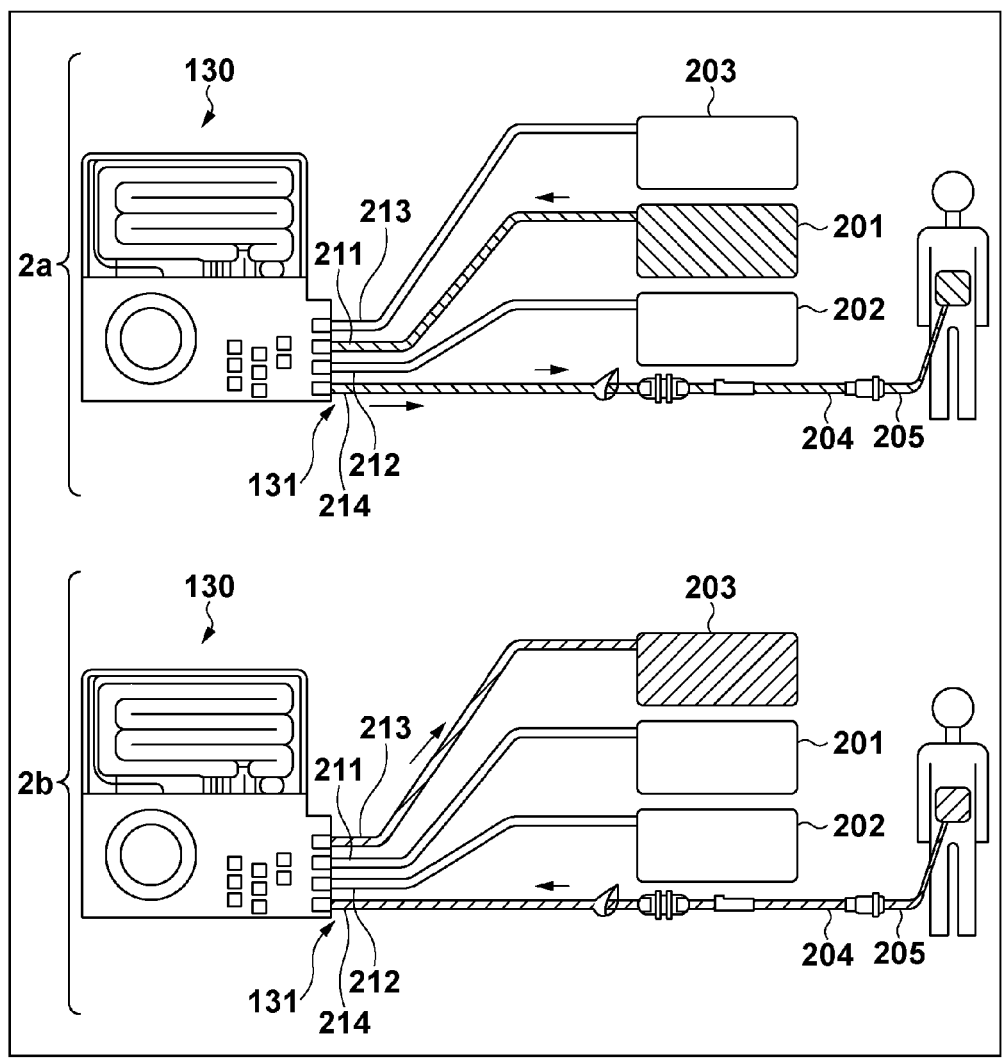
FIG. 2 shows how a dialysis solution bag, a transfer tube set to which a dialysis catheter is connected, and a drainage tank are connected to a cassette and the flows of a dialysis solution at the time of injection and at the time of drainage.

When the patient inputs an instruction to start infusion after mounting the cassette 130 in the peritoneal dialysis apparatus 100 (not shown in FIG. 2), the peritoneal dialysis apparatus 100 switches the flow paths in the cassette 130 to infuse the dialysis solution contained in the dialysis solution bag 201 to the dialysis catheter 205 through the cassette 130, as indicated by 2a in FIG. 2. With this operation, the dialysis solution is injected into the patient.

When the patient inputs an instruction to start drainage, the peritoneal dialysis apparatus 100 switches the flow paths in the cassette 130 to discharge the dialysis solution in the peritoneal cavity of the patient through the dialysis catheter 205 and infuse the solution to the drainage tank 203 through the cassette 130, as indicated by 2b in FIG. 2. With this operation, the dialysis solution is discharged from the patient.

3. Arrangement of Cassette 130

Figure 3:
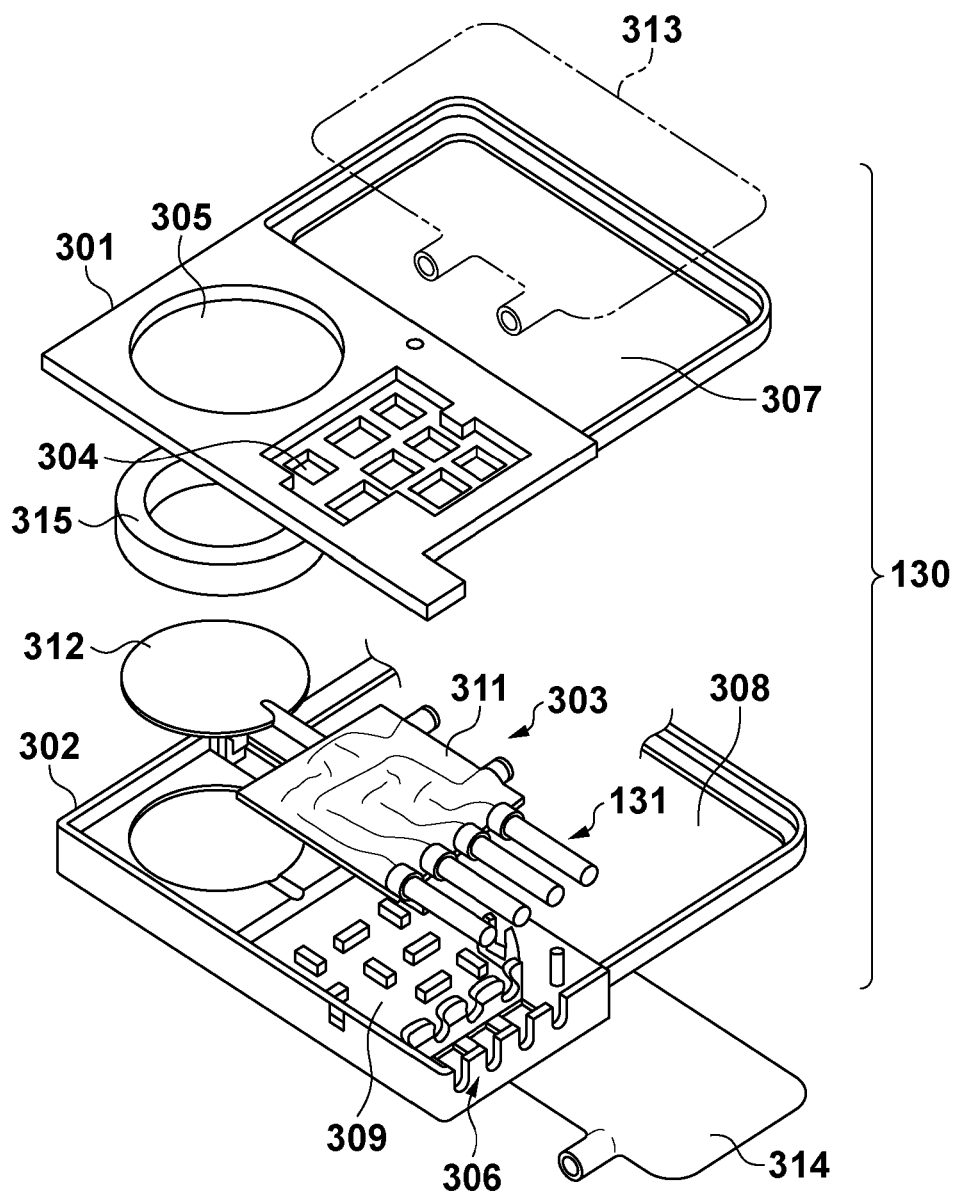
FIG. 3 is a view showing the arrangement of the cassette mounted in the peritoneal dialysis apparatus 100.

The arrangement of the cassette 130 mounted in the cassette mounting portion 112 is described next. FIG. 3 is a view showing the arrangement of the cassette 130.

As shown in FIG. 3, the cassette 130 includes an upper cassette housing 301 and a lower cassette housing 302. A flow path switching unit 303 is provided between the upper cassette housing 301 and the lower cassette housing 302.

The flow path switching unit 303 is configured such that a diaphragm pump 312, the connection unit 131, an upper warmer unit 313, and a lower warmer unit 314 are connected outside a flow path unit 311 in which infusing paths, drainage paths, and the like are inserted.

The flow path unit 311 is placed on a fixing portion 309 of the lower cassette housing 302. The infusing paths, drainage paths, and the like are supported by support protrusions provided on the fixing portion 309. A plurality of opening portions 304 are provided in the upper cassette housing 301 at positions facing the fixing portion 309 on which the flow path unit 311 is placed. With this arrangement, actuating a clamp in the peritoneal dialysis apparatus 100 while the cassette 130 is mounted in it will clamp the infusion and drainage paths in the flow path unit 311 at predetermined positions through the opening portions 304.

A flange member 315 is provided on the circumference of the diaphragm pump 312. The flange member 315 is configured to be externally pressed through an opening portion 305 provided in the upper cassette housing 301. With this arrangement, when the flange member 315 is repeatedly pressed by actuating the pumping actuation unit of the peritoneal dialysis apparatus 100 while the cassette 130 is mounted in the peritoneal dialysis apparatus 100, the diaphragm pump 312 repeatedly expands and contracts. This will control the infusion of a dialysis solution.

The connection unit 131 is fitted in an opening portion 306 formed in a side surface of the lower cassette housing 302 and is fixed with its distal end portion protruding outside the cassette 130.

The upper warmer unit 313 and the lower warmer unit 314 are connected to the flow path unit 311 while being connected to each other. For this reason, the dialysis solution in the flow path unit 311 passes through the lower warmer unit 314 and the upper warmer unit 313 and then returns to the flow path unit 311.

Note that the upper warmer unit 313 and the lower warmer unit 314 are respectively placed at positions corresponding to an opening portion 307 in the upper cassette housing 301 and an opening portion 308 in the lower cassette housing 302 while being exposed outside the cassette 130. This allows the surface heater of the peritoneal dialysis apparatus 100 to externally warm the upper warmer unit 313 and the lower warmer unit 314 while the cassette 130 is mounted in the peritoneal dialysis apparatus 100.

4. Flow Path Arrangement of Flow Path Switching Unit 303 of Cassette 130

Figure 4:
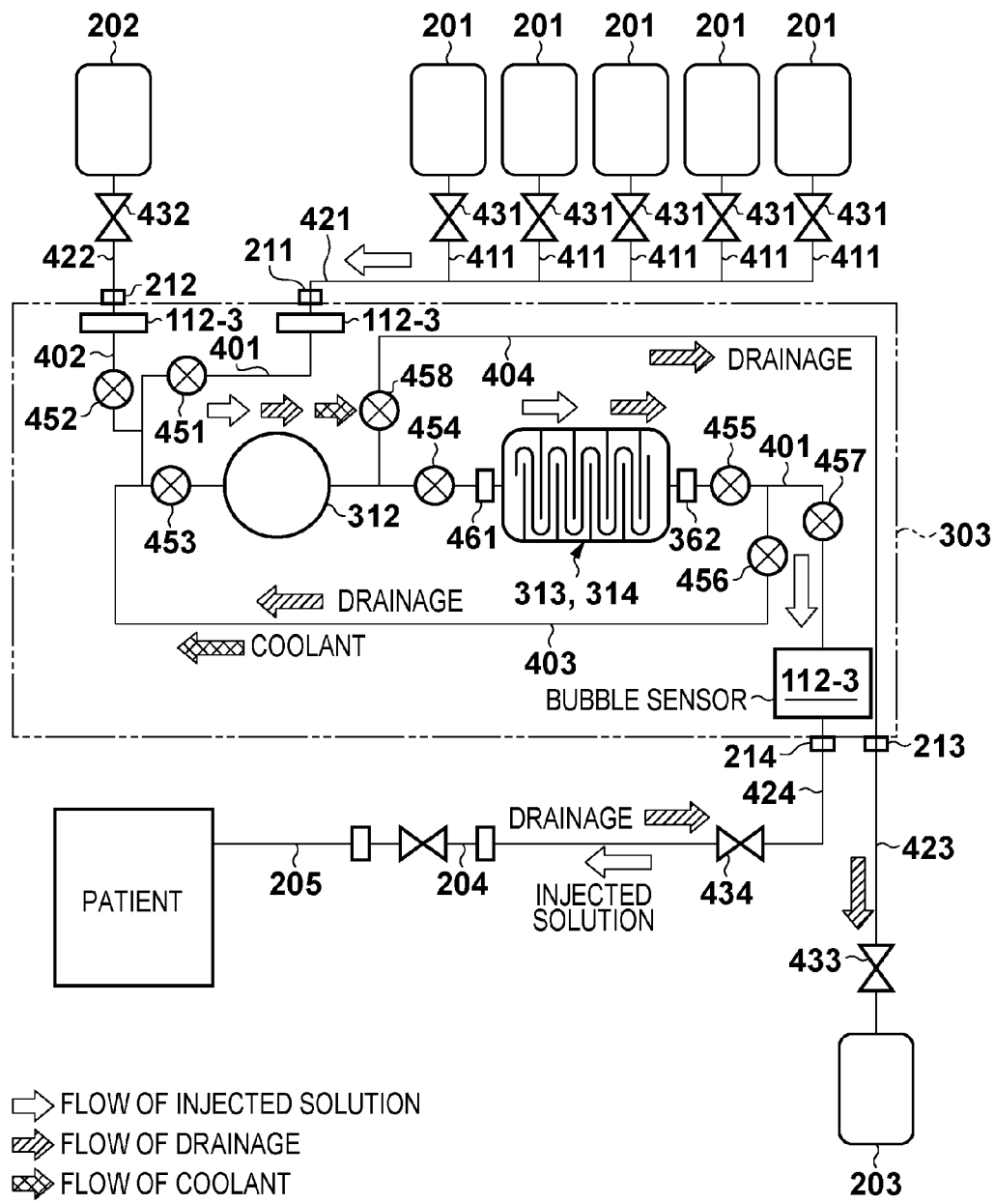
FIG. 4 is a view for explaining the arrangement of flow paths in the cassette.

The flow path arrangement of the flow path switching unit 303 of the cassette 130 is described next. FIG. 4 is a view for explaining the flow path arrangement of the flow path switching unit 303 of the cassette 130. For the sake of easy comprehension of the flows of a dialysis solution and drainage, FIG. 4 shows a state in which the dialysis solution bag 201, the additional dialysis solution bag 202, the drainage tank 203, and the transfer tube set 204 to which the dialysis catheter 205 is connected are connected to the respective connecting portions.

As shown in FIG. 4, the dialysis solution bags 201 are connected to an infusion tube 421 through branch tubes 411. The dialysis solution in each dialysis solution bag 201 is collected in the infusion tube 421 through the branch tube 411. Note that each branch tube 411 is provided with a clamp 431 which opens/closes the tube.

Likewise, the additional dialysis solution bag 202 is connected to an additional infusion tube 422. The dialysis solution in the additional dialysis solution bag 202 is provided to the additional infusion tube 422. Note that the additional infusion tube 422 is provided with a clamp 432 which opens/closes the tube.

The infusion tube 421 is also connected to an infusion path 401 through the connecting portion 211. A first clamp 451 is provided on the infusion path 401 (on the peritoneal dialysis apparatus 100 side) near the connecting portion 211 so that the infusion path 401 can be clamped at the position shown in FIG. 4.

A second clamp 452 is provided on an additional infusion path 402 (on the peritoneal dialysis apparatus 100 side) near the connecting portion 212 so that the additional infusion path 402 can be clamped at the position shown in FIG. 4.

The bubble sensors 112-3 are respectively placed on the infusion path 401 between the connecting portion 211 and the clamp position of the first clamp 451 and on the additional infusion path 402 between the connecting portion 212 and the clamp position of the second clamp 452. With this arrangement, the peritoneal dialysis apparatus 100 monitors the presence/absence of bubbles in a dialysis solution infused into the flow path switching unit 303.

The dialysis solution supplied to the infusion path 401 or the additional infusion path 402 is supplied to the diaphragm pump 312. Note that a third clamp 453 is provided on the infusion path 401 (on the peritoneal dialysis apparatus 100 side) in front of the diaphragm pump 312 so that the infusion path 401 can be clamped at the position shown in FIG. 4. In addition, a fourth clamp 454 is provided on the infusion path 401 (on the peritoneal dialysis apparatus 100 side) on the exit side of the diaphragm pump 312 so that the infusion path 401 can be clamped at the position shown in FIG. 4.

The peritoneal dialysis apparatus 100 actuates the pumping actuation unit to cause the diaphragm pump 312 to repeatedly contract and expand. At this time, it is possible to control the infusion direction of a dialysis solution by properly controlling clamping/unclamping of the third clamp 453 and fourth clamp 454.

An inlet solution temperature sensor 461 is provided in the infusion path 401 of the diaphragm pump 312 to detect the temperature of the dialysis solution infused to the lower warmer unit 314.

Likewise, an outlet solution temperature sensor 462 is provided on the exit side of the upper warmer unit 313 to detect the temperature of the dialysis solution infused from the upper warmer unit 313. A fifth clamp 455 is provided on the infusion path 401 (on the peritoneal dialysis apparatus 100 side) on the exit side of the upper warmer unit 313 so that the infusion path 401 can be clamped at the position shown in FIG. 4.

The infusion path 401 branches off on the downstream side of the fifth clamp 455. A bypass 403 is connected to the infusion path 401 in front of the clamp position of the third clamp 453. A sixth clamp 456 is provided on the bypass 403 (on the peritoneal dialysis apparatus 100 side) so that the bypass 403 can be clamped at the position shown in FIG. 4.

The infusion path 401 is connected to an infusion/drainage tub 424 through the connecting portion 214. A seventh clamp 457 is provided on the infusion path 401 (on the peritoneal dialysis apparatus 100 side) on the way to the position where it is connected to the connecting portion 214 so that the infusion path 401 can be clamped at the position shown in FIG. 4. In addition, the bubble sensor 112-3 is placed on the infusion path 401 (on the peritoneal dialysis apparatus 100 side) near the connecting portion 214 to monitor the presence/absence of bubbles in the dialysis solution infused from the flow path switching unit 303 to the dialysis catheter 205.

The infusion/drainage tube 424 is connected to the transfer tube set 204 through a clamp 434, and is further connected to the dialysis catheter 205 to be dwelled in the peritoneal cavity of the patient.

On the other hand, a drainage path 404 branching from the infusion path 401 is connected to a drainage tube 423 in the connecting portion 213 at a position between the diaphragm pump 312 and the clamp position of the fourth clamp 454. The drainage tube 423 is further connected to the drainage tank 203. Note that an eighth clamp 458 is provided on the drainage path 404 (on the peritoneal dialysis apparatus 100) so that the drainage path 404 can be clamped at the position shown in FIG. 4. A clamp 433 is provided on the drainage tube 423.

5. Flows of Dialysis Solution Injected/Discharged in Peritoneal Dialysis Apparatus The flows of the dialysis solution injected/discharged in the flow path switching unit 303 under the control of the first to eighth clamps 451 to 458 by the peritoneal dialysis apparatus 100 is described next with reference to the flow path arrangement shown in FIG. 4. The peritoneal dialysis apparatus 100 switches between the state in which the dialysis solution in the dialysis solution bag 201 (and/or the additional dialysis solution bag 202) is infused to the dialysis catheter 205, that is, the infusion state in which the dialysis solution is injected into the peritoneum of the patient, and the state in which the drainage discharged from the dialysis catheter 205 is infused to the drainage tank 203, that is, the drainage state in which the dialysis solution is discharged from the peritoneum of the patient. The flows of a dialysis solution in the flow path switching unit 303 is described separately with reference to the infusion state and the drainage state.

(1) Flow of Dialysis Solution in Infusion State

When injecting the dialysis solution contained in the dialysis solution bag 201 into the peritoneum of the patient, the apparatus fully opens the clamp 432, and causes the second clamp 452 to clamp the additional infusion path 402. The apparatus then fully opens the clamp 431 and causes the first clamp 451 to unclamp the infusion path 401.

This makes only the dialysis solution in the dialysis solution bag 201 be supplied to the infusion path 401 through the branch tube 411 and the infusion tube 421. The apparatus then switches the third clamp 453 and fourth clamp 454 on the infusion path 401 between the clamp position and the unclamp position in accordance with pumping actuation for the diaphragm pump 312, thereby infusing the dialysis solution to the dialysis catheter 205.

At this time, since the eighth clamp 458 is clamped, the dialysis solution does not flow in the direction of the drainage path 404 but flows in only the infusion path 401.

In addition, the infusion path 401 is clamped by the fifth clamp 455 and the seventh clamp 457, and the bypass 403 is clamped by the sixth clamp 456. This causes the dialysis solution supplied by the diaphragm pump 312 to be infused to the infusion/drainage tub 424 after being warmed by the lower warmer unit 314 and the upper warmer unit 313.

If the temperature of the dialysis solution warmed by the lower warmer unit 314 and the upper warmer unit 313 exceeds a predetermined temperature, the seventh clamp 457 clamps the infusion path 401 and the sixth clamp 456 unclamps the bypass 403 to supply the dialysis solution to the bypass 403 in order to cool the dialysis solution. At this time, the apparatus stops warming the lower warmer unit 314 and the upper warmer unit 313, and the bypass 403 causes the dialysis solution to circulate around the lower warmer unit 314 and the upper warmer unit 313. As a result, the dialysis solution is cooled.

After the dialysis solution is cooled, the seventh clamp 457 unclamps the infusion path 401 again and the sixth clamp 456 clamps the bypass 403 to supply the dialysis solution to the infusion/drainage tub 424. At this time, the clamp 434 on the infusion/drainage tub 424 is fully opened. This makes the supplied dialysis solution reach the dialysis catheter 205 through the transfer tube set 204.

(2) Flow of Peritoneal Dialysis in Drainage State

The flow of a drainage in a case in which a dialysis solution is discharged from the peritoneal cavity of the patient is described next. The drainage discharged from the dialysis catheter 205 is supplied to the infusion path 401 through the transfer tube set 204, the infusion/drainage tub 424, and the connecting portion 214. At the time of drainage, the clamp 434 is fully opened, and the seventh clamp 457, sixth clamp 456, third clamp 453, and eighth clamp 458 unclamp part of the infusion path 401, the bypass 403, and the drainage path 404, while the fifth clamp 455, fourth clamp 454, first clamp 451, and second clamp 452 clamp part of the infusion path 401 and the additional infusion path 402.

For this reason, the drainage supplied into the infusion path 401 is supplied to the drainage path 404 through the bypass 403 and is supplied to the drainage tank 203 through the connecting portion 213 and the drainage tube 423. Note that the third clamp 453 and the eighth clamp 458 are switched between the clamp and unclamp positions in accordance with pumping actuation for the diaphragm pump 312 to supply the drainage of dialysis solution to the drainage tank 203.

6. Functional Arrangement of Peritoneal Dialysis Apparatus

Figure 5:
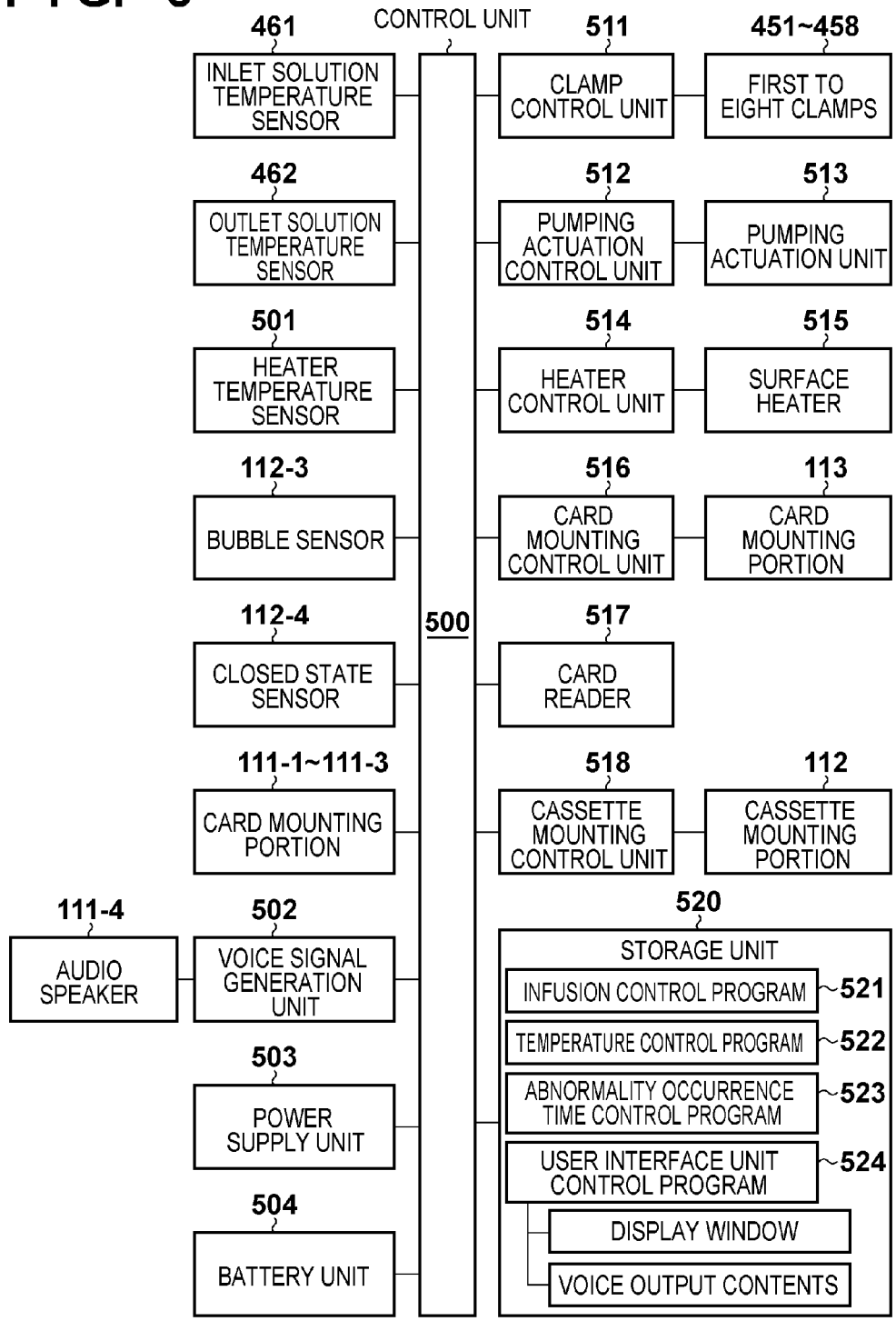
FIG. 5 is a block diagram showing the functional arrangement of the peritoneal dialysis apparatus 100.

The functional arrangement of the peritoneal dialysis apparatus 100 is described next. FIG. 5 is a block diagram showing the functional arrangement of the peritoneal dialysis apparatus 100. Note that the same reference numerals denote the same components as those described above, and a detailed description of them is omitted.

Referring to FIG. 5, reference numeral 500 denotes a control unit including a CPU (Central Processing Unit) such as a microcomputer, a ROM storing control programs for the overall apparatus which are executed by the CPU and various kinds of data, and a RAM serving as a work area and temporarily storing measurement data and various kinds of data. The control unit 500 performs determination and control in each operation step in the overall peritoneal dialysis apparatus 100. The inlet solution temperature sensor 461 measures the temperature of a dialysis solution at the inlet of the lower warmer unit 314 which warms the dialysis solution supplied into the mounted cassette 130, and outputs the resultant data to the control unit 500. The outlet solution temperature sensor 462 measures the temperature of a dialysis solution at the outlet of the upper warmer unit 313, and outputs the resultant data to the control unit 500. Reference numeral 501 denotes a heater temperature sensor which measures the temperature of a surface heater 515 which warms a dialysis solution in the warmer unit.

Reference numeral 502 denotes a voice signal generation unit which generates a voice signal to be output from the audio speaker 111-4 based on an instruction from the control unit 500.

Reference numeral 503 denotes a power supply unit which supplies power to the control unit 500 and the respective units connected to the control unit 500; and 504, a battery unit which supplies power to the control unit 500 and the respective units connected to the control unit 500 when the supply of power from the power supply unit 503 is shut off by a power failure or the like.

Reference numeral 511 denotes a clamp control unit which switches the flow path states (the infusion state and the drainage state) in the cassette 130 by controlling the operations of the first to eighth clamps 451 to 458 which clamp flow paths in the mounted cassette 130.

Reference numeral 512 denotes a pumping actuation control unit which controls a pumping actuation unit 513 which performs pumping operation for the diaphragm pump 312 in the mounted cassette 130. Note that the control unit 500 controls the infusion direction in the cassette 130 by controlling clamping/unclamping of the clamps (third clamp 453, fourth clamp 454, and eighth clamp 458) located before and after the diaphragm pump 312 in association with the pumping operation of the pumping actuation unit 513.

Reference numeral 514 denotes a heater control unit which controls the operation of the surface heater 515 which warms the dialysis solution supplied in the mounted cassette 130 based on outputs from the inlet solution temperature sensor 461, the outlet solution temperature sensor 462, and the heater temperature sensor 501, thereby controlling the temperature of the dialysis solution injected into the peritoneum of the patient within a predetermined temperature range.

Reference numeral 516 denotes a card mounting control unit which detects the mounting of the card 140 in the card mounting portion 113, and notifies the control unit 500 of the mounting of the card. Upon receiving a notification of a remove instruction from the control unit 500, the card mounting control unit 516 performs control to eject the mounted card 140. Reference numeral 517 denotes a card reader which reads, for example, information about the patient recorded on the card 140 mounted in the card mounting portion 113 and notifies the control unit 500 of the read information.

Reference numeral 518 denotes a cassette mounting control unit which detects the mounting of the cassette 130 in the cassette mounting portion 112, and notifies the control unit 500 of the mounting of the cassette 130. Upon receiving a remove instruction from the control unit 500, the cassette mounting control unit 518 performs control to eject the mounted cassette 130.

Reference numeral 520 denotes a storage unit which stores outputs from the respective sensors 461, 462, 501, 112-3, and 112-4 and set values and the like input via operation display units (start instruction unit 111-1, stop instruction unit 111-2, and display unit 111-3). The storage unit 520 also stores programs 521 to 524 for controlling the operations of the respective units 111-1 to 111-3, 502 to 504, 511, 512, 514, and 516 to 518. The storage unit 520 further stores display windows which can be displayed by the display unit 111-3, voice output contents which can be output from the audio speaker 111-4, and the like.

An infusion control program 521 operates the first to eighth clamps 451 to 458 and the pumping actuation unit 513 by outputting control signals to the clamp control unit 511 and the pumping actuation control unit 512 based on instructions from the operation display units 111-1 to 111-3.

A temperature control program 522 operates the surface heater 515 by outputting a control signal to the heater control unit 514 based on outputs from the inlet solution temperature sensor 461, the outlet solution temperature sensor 462, and the heater temperature sensor 501.

An abnormality occurrence time control program 523 determines various kinds of abnormalities and notifies determination results when, for example, the bubble sensor 112-3 detects bubbles and the supply of power from the power supply unit 503 stops due to a power failure or the like. Note that this program also issues instructions to warm, stop infusion, and switch to the battery unit 504.

A user interface unit control program 524 (display control unit) displays a display window on the display unit 111-3 and outputs voice output contents to be output from the audio speaker 111-4 to the voice signal generation unit 502. The user interface unit control program 524 further accepts instructions input via the operation display units 111-1 to 111-3. Note that of the respective types of functions implemented when the control unit 500 executes the user interface unit control program 524, the operation procedure explanation function, which is a characteristic function of the peritoneal dialysis apparatus 100 according to this embodiment, is described in detail below.

7. Description of Operation Procedure Explanation Function

A characteristic feature of the operation procedure explanation function of the peritoneal dialysis apparatus 100 according to this embodiment is that four explanation modes are prepared in accordance with the levels of proficiency in operation of patients to allow a patient to select one of the modes in accordance with his/her level of proficiency, in consideration of the fact that the respective patients vary in level of proficiency in operation procedures (level of proficiency in operation).

In addition, in consideration of the fact that even a patient having a high level of proficiency in operation sometimes needs a detailed explanation of an operation procedure associated with a specific operation content, this function has the following characteristic feature. Even if a patient selects an explanation mode for patients with a high level of proficiency in operation procedures, and the function starts to explain an operation procedure, the function switches the explanation mode to an explanation mode for patients having a low level of proficiency in operation procedures when explaining a specific operation procedure, and then returns to the explanation mode for patients having the high level of proficiency in operation procedures again to continue the remaining explanation of the operation procedures after the explanation of the specific operation procedure.

(1) Description of Explanation Modes

Figure 6:
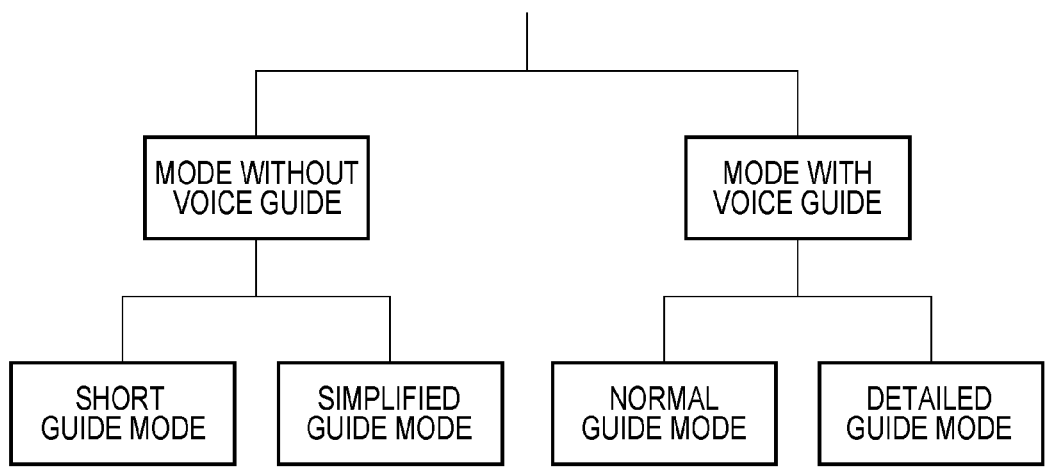
FIG. 6 is a view showing the relationship among selectable explanation modes in the peritoneal dialysis apparatus 100.

FIG. 6 is a view showing the explanation modes of four levels of the operation procedure explanation function of the peritoneal dialysis apparatus 100 according to this embodiment. As shown in FIG. 6, the explanation modes include a short guide mode, a simplified guide mode, a normal guide mode, and a detailed guide mode. In this case, the hierarchical levels descend in the order of the short guide mode, the simplified guide mode, the normal guide mode, and the detailed guide mode (that is, the short guide mode is at the highest level, and the detailed guide mode is at the lowest level).

The detailed guide mode is an explanation mode for patients who perform peritoneal dialysis by using the peritoneal dialysis apparatus 100 for the first time. In this explanation mode, the apparatus explains each operation procedure by using one window with a combination of graphic representation (texts and pictures) and voice.

The normal guide mode is an explanation mode set as a default in the peritoneal dialysis apparatus 100. In this explanation mode, the apparatus explains a plurality of operation procedures as one group by using one window with a combination of graphic representation (texts and pictures) and voice in accordance with the purpose of preparatory operation.

The simplified guide mode is an explanation mode of further grouping a plurality of operation procedures, which are grouped in accordance with the purpose of operation in the normal guide mode, into one group, and explaining it by using one window with texts while reading them aloud. This is an explanation mode for patients having a high level of proficiency in operation and healthcare personnel.

The short guide mode is an explanation mode of displaying a plurality of operation procedures by using one window with texts while reading them aloud. This is an explanation mode for patients and healthcare personnel who have a higher level of proficiency in operation than those suited to the simplified guide mode.

In this mode arrangement, a patient can receive an explanation in accordance with his/her level of proficiency in operation by pressing the start instruction unit 111-1 and then selecting one of the explanation modes of the four levels displayed on the display unit 111-3 in accordance with his/her level of proficiency in operation. According to defaults of the short guide mode and simplified guide mode, the apparatus does not explain with voice in consideration of the fact that some patients feel annoying when receiving an explanation with texts and voice.

(2) Outline of Window Transition in Each Explanation Mode

Figure 7A:
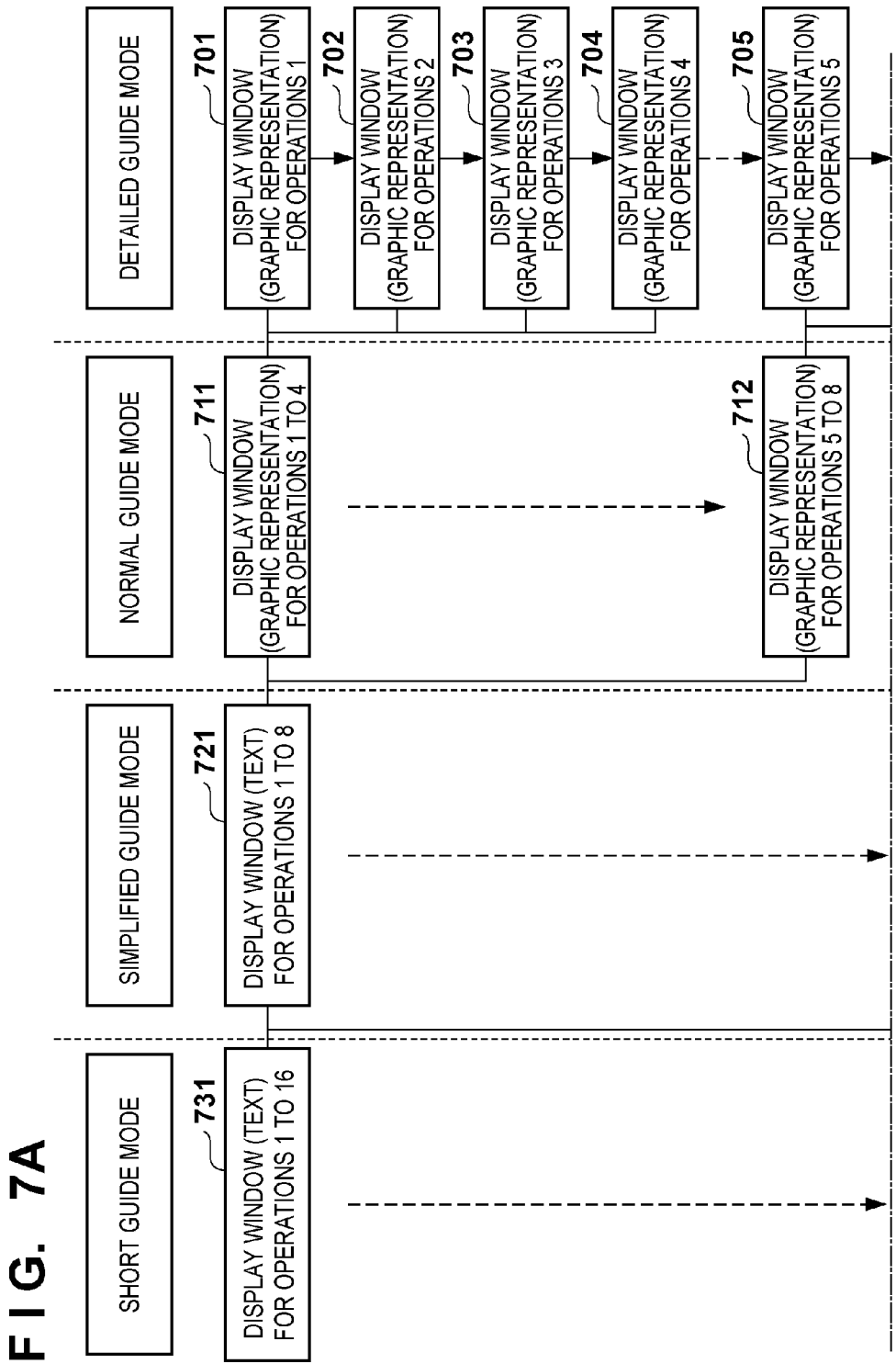
FIGS. 7A and 7B are views showing the transition of display windows in the respective explanation modes.
Figure 7B:
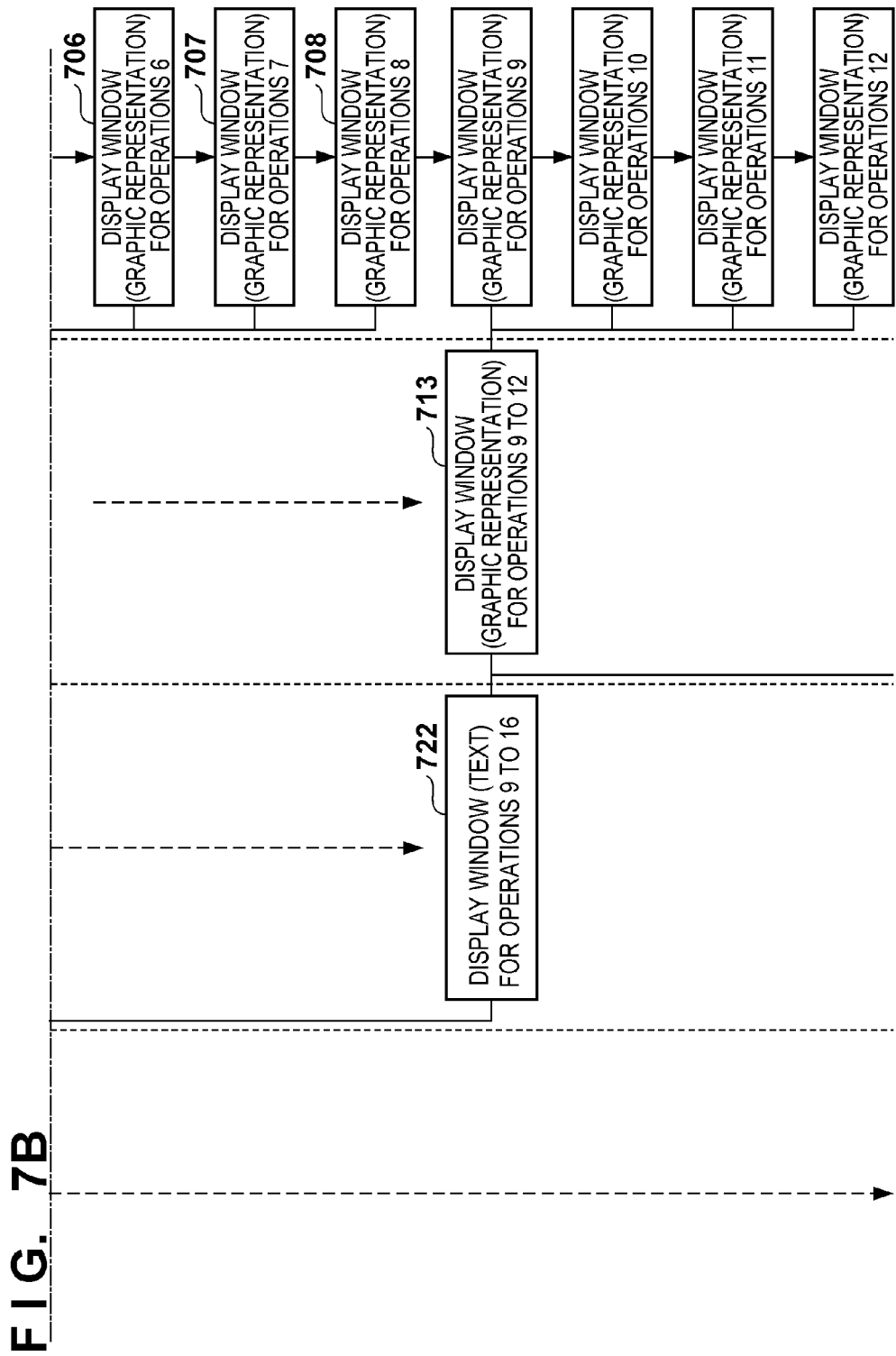
Figure 9A:
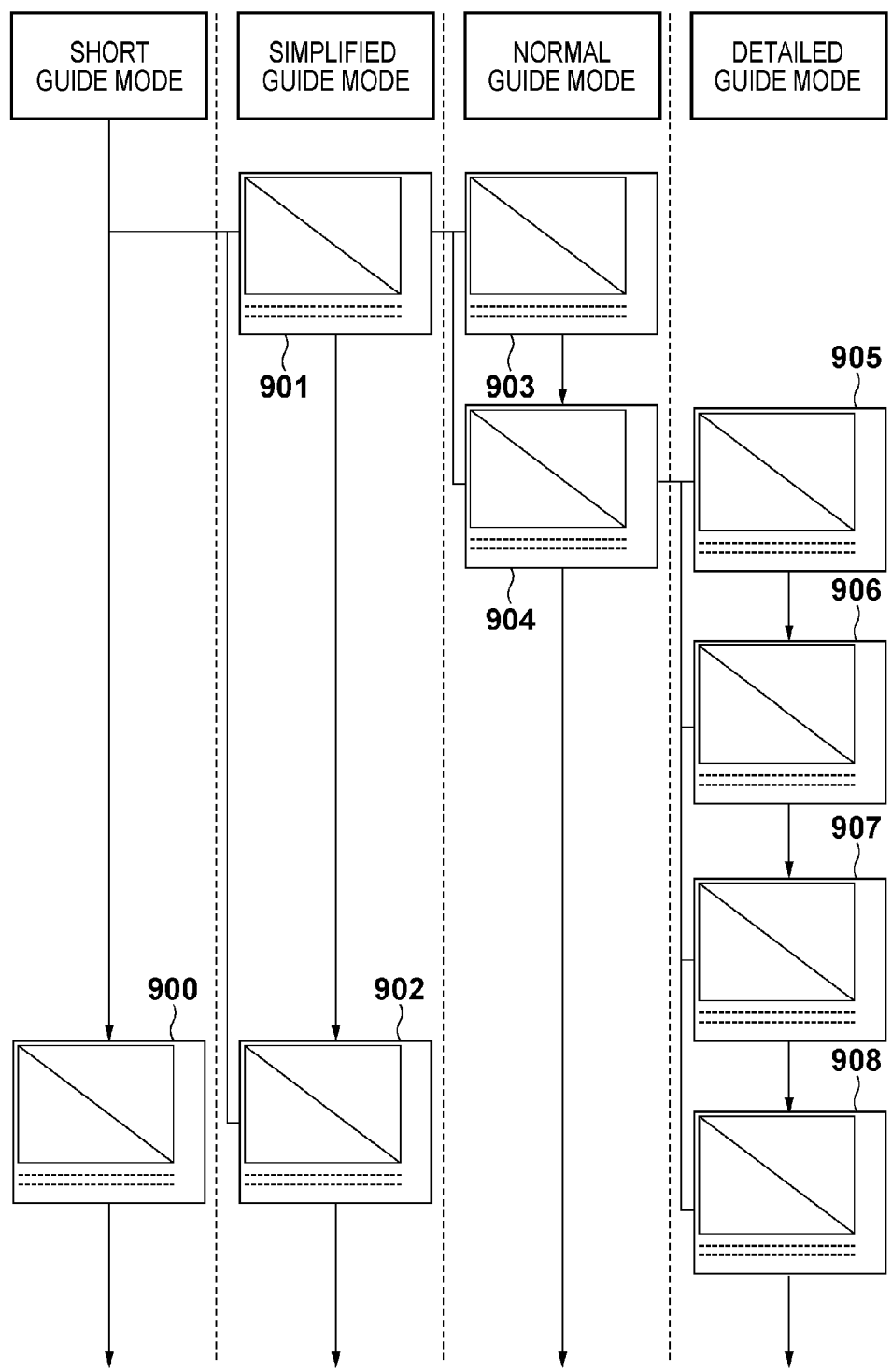

FIGS. 7A and 7B are conceptual views for explaining an outline of window transition in each explanation mode. As shown in FIGS. 7A and 7B, in the peritoneal dialysis apparatus 100 according to this embodiment, display windows are prepared for each explanation mode. Explanation contents on display windows classified to each explanation mode have a hierarchical structure relative to explanation contents on display windows classified to other explanation modes, which have the same operation purposes. For this reason, the storage unit 520 stores the way of classifying the respective display windows to the specific explanation modes and the hierarchical relationship between the respective hierarchical display windows.

Referring to FIGS. 7A and 7B, reference numerals 701 to 708 denote display windows classified to the detailed guide mode. The display windows 701 to 704 display graphic representations for explaining operation procedures 1 to 4. The display windows 705 to 708 display graphic representations for explaining operation procedures 5 to 8. Note that the display windows 701 to 704 differ in operation purpose from the display windows 705 to 708.

Reference numerals 711 and 712 denote display windows classified to the normal guide mode. The display window 711 displays a graphic representation of operation procedures 1 to 4 as one group. The display window 712 displays a graphic representation of operation procedures 5 to 8 as one group. Note that the display windows 701 to 704 in the detailed guide mode are associated with the display window 711 in the normal guide mode, and the display windows 705 to 708 in the detailed guide mode are associated with the display window 712 in the normal guide mode.

Reference numeral 721 denotes a display window classified to the simplified guide mode, which explains the contents of operation procedures 1 to 8 as one group by using texts; and 731, a display window classified to the short guide mode, which explains the operation purposes of operation procedures 1 to 8 and of operation procedures 9 to 16 by using texts.

Under the hierarchical structure described above, when the patient operates the touch panel of the display unit 111-3 to activate the operation procedure explanation function, the display unit 111-3 displays the characters "short guide mode", "simplified guide mode", "normal guide mode", and "detailed guide mode" in the form of a list. When the patient selects "short guide mode" by input via the display unit 111-3, display window transition occurs in the order of the display window 731, a display window 732 (not shown), . . . .

Likewise, when the patient operates the display unit 111-3 and selects "simplified guide mode" by the first input via the display unit 111-3, display window transition occurs in the order of the display window 721, a display window 722, . . . as the patient operates the button "next". When the patient operates the touch panel of the display unit 111-3 and selects "normal guide mode", display window transition occurs in the order of the display window 711, the display window 712, . . . . When the patient operates the touch panel of the display unit 111-3 and selects "detailed guide mode", display window transition occurs in the order of the display window 701, the display window 702, the display window 703, the display window 704, the display window 705, a display window 706, display window 707, display window 708, . . . .

Assume that after the patient operates the touch panel of the display unit 111-3 to select "normal guide mode", he/she needs to receive a detailed explanation of an operation procedure while the display window 711 is displayed. In this case, the peritoneal dialysis apparatus 100 according to this embodiment is configured to display the display window 701 in "detailed guide mode" one level lower than "normal guide mode" upon accepting an instruction to give a detailed explanation.

By operating the button "next" displayed on the display unit 111-3 while the display window 701 is displayed under this circumstance, the patient can proceed with display window 702→display window 703→display window 704. Alternatively, operating the button "return" displayed on the touch panel of the display unit 111-3 makes it possible to return to the display window 711 one level higher than the current display window. Note that when display transition proceeds up to the display window 704, the apparatus automatically returns to the display window 711.

Likewise, assume that after the patient operates the display unit 111-3 to select "simplified guide mode", he/she needs to receive a detailed explanation of an operation procedure while the display window 721 is displayed. In this case, the peritoneal dialysis apparatus 100 according to this embodiment is configured to display the display window 711 upon accepting an instruction to give a detailed explanation.

By operating the button "next" displayed on the display unit 111-3 while the display window 711 in "normal guide mode" is displayed under this circumstance, the patient can proceed to the display window 712. Alternatively, operating the button "return" displayed on the touch panel of the display unit 111-3 makes it possible to return to the display window 721. In addition, operating the button "next" displayed on the touch panel of the display unit 111-3 can proceed to the display window 701. Note that when the patient proceeds to the display window 701, operating the button "next" displayed on the touch panel of the display unit 111-3 allows to proceed to display window 702→display window 703→display window 704. Alternatively, operating the button "return" displayed on the touch panel of the display unit 111-3 allows to return to the display window 711 on the way. When display transition proceeds like display window 702→display window 703→display window 704, the apparatus automatically returns to the display window 711.

As described above, when the patient selects a predetermined explanation mode, the peritoneal dialysis apparatus 100 according to this embodiment can sequentially display windows classified to the explanation mode. On the other hand, at an arbitrary timing, the apparatus can make transition to a display window which is classified to an explanation mode lower in level than the current explanation mode and is the first window of the display windows associated with the display window displayed on the display unit 111-3.

In addition, when the apparatus has made transition to a display window classified to the explanation mode of a lower level, it is possible to make transition, at an arbitrary timing, to a display window which is classified to the explanation mode one level higher than the current explanation mode to which the display window displayed on the display unit 111-3 is classified and is a display window associated with the display window currently displayed on the display unit 111-3.

Furthermore, when the apparatus has made transition to a display window classified to an explanation mode of a lower level and has proceeded up to the last window of all the display windows classified to the explanation mode of the lower level and associated with the display window before the transition, the apparatus can automatically return to the display window before the transition.

As described above, the peritoneal dialysis apparatus 100 according to this embodiment is configured to display display windows in accordance with the level of proficiency in operation procedure of a patient when he/she selects one of the explanation modes in accordance with his/her own level of proficiency in operation. That is, the apparatus is very convenient to the patient.

In addition, the apparatus is configured to switch to an explanation mode for patients having a low level of proficiency in operation at the time of explanation of a specific operation procedure and then return to the explanation mode for patients having a high level of proficiency in operation after the completion of the explanation of the specific operation procedure so as to allow the patient to continuously receive the remaining explanation of operation procedures. That is, the apparatus is very convenient to patients of various levels.

8. Procedure for Window Transition Processing

The transition of display windows in the operation procedure explanation function, which has been described in detail with reference to FIGS. 7A and 7B, is described again with reference to the flowchart of FIG. 8.

In step S801, the apparatus recognizes the explanation mode selected by the patient. In step S802, the apparatus checks the instruction contents input by the patient to make display window transition.

If the instruction content input by the patient is an instruction to make transition to the next display window by operating the button "next" displayed on the touch panel of the display unit 111-3, the process advances to step S803 to make transition to the next display window in the explanation mode to which the display window currently displayed on the display unit 111-3 is classified.

If the instruction content input when the patient has operated the button "next" displayed on the touch panel of the display unit 111-3 is an instruction to make transition to a display window displaying a more detailed explanation, the process advances to step S804 to make transition to a display window which is classified to an explanation mode one level lower than the explanation mode to which the display window currently displayed on the display unit 111-3 is classified and is the first window of the display windows associated with the display window before the transition.

If the instruction content input by the patient is an instruction to make transition to the display window before the transition by operating the button "next" displayed on the touch panel of the display unit 111-3, the process advances to step S805. In step S805, the apparatus determines whether the explanation mode to which the display window currently displayed on the display unit 111-3 is classified is the selected explanation mode. If the apparatus determines in step S805 that the explanation mode is not the selected explanation mode, the process advances to step S806 to make transition to a display window classified to the explanation mode one level higher than the explanation mode to which the display window currently displayed on the display unit 111-3 is classified. If the apparatus determines that the explanation mode is the selected explanation mode, the process directly advances to step S807 (that is, the apparatus is configured to return to the initially selected explanation mode but be inhibited from shifting to an explanation mode higher in level than the initially selected explanation mode).

Upon completion of display of the display window to which transition has been made in step S803, S804, or S806, the apparatus determines in step S807 whether the explanation mode to which the display window at the completion of display is classified is the selected explanation mode. If the apparatus determines that the explanation mode is the selected explanation mode, the process returns to step S802.

If the apparatus determines that the explanation mode is not the selected explanation mode, the process advances to step S808 to determine whether the display window at the completion of display is the last window of all the display windows associated with the display window before the transition. If the apparatus determines that the display window is not the last display window, the process returns to step S802. If the apparatus determines that the display window is the last display window, the process advances to step S809 to automatically make transition to a display window classified to the explanation mode one level higher than the explanation mode to which the display window at the completion of display is classified. The process then returns to step S802.

9. Example

FIGS. 9A to 9D are views showing an example of each display window displayed on the display unit 111-3 of the peritoneal dialysis apparatus 100 according to this embodiment. The respective display windows in "short guide mode", "simplified guide mode", "normal guide mode", and "detailed guide mode" shown in FIGS. 9A to 9D shift according to the flowchart shown in FIG. 8.

As is obvious from the above description, the peritoneal dialysis apparatus 100 according to this embodiment can give explanations corresponding to the levels of proficiency in operation when explaining to a patient about operation procedures.

Second Embodiment

The first embodiment is configured to improve convenience to patients by preparing the explanation modes of the four levels in consideration of the levels of proficiency in operation of the respective patients. However, the present invention is not limited to this. For example, it is possible to improve convenience to patients by improving the operability of each display window.

More specifically, while the apparatus is basically configured to make a patient operate the touch panel of the display unit 111-3 when proceeding from the currently display window to the next display window, the apparatus may be configured to make transition to the next display window by voice recognition from a display window explaining an operation procedure when both the hands of the patient are occupied, and hence it is difficult for him/her to operate the touch panel. Alternatively, the apparatus may be configured to automatically make transition to the next display window after the lapse of a predetermined period of time.

In addition, the first embodiment is configured to make each patient select an explanation mode in accordance with his/her level of proficiency in operation. However, the present invention is not limited to this. For example, the apparatus may be configured to change the contents of a display window to be displayed depending on the disease conditions of patients even if they have the same level of proficiency in operation. More specifically, the apparatus may be configured to display display windows customized for each patient, for example, being inhibited from operating predetermined items on display windows, based on the information about the patient recorded on the card 140.

The first embodiment has been described on the premise that a dialysis solution is injected and discharged immediately after preparatory operation for peritoneal dialysis is complete. However, the present invention is not limited to this. For example, the apparatus may be configured to make a patient perform preparatory operation for peritoneal dialysis in advance so as to allow him/her to start injecting a dialysis solution at bedtime or the like. More specifically, the operation procedure explanation function is provided with a standby mode. Upon completion of preparatory operation for peritoneal dialysis, the apparatus shifts to the standby mode to be kept ready for the start of injection of a dialysis solution until the patient inputs an instruction to start injecting the dialysis solution.

Although the first embodiment has not made any specific reference to infusion rates at the time of injection of a dialysis solution and at the time of discharge of the dialysis solution, the apparatus may be configured to control the infusion rate at the time of injection of a dialysis solution to a rate lower than that at the time of discharge of the dialysis solution. Alternatively, the apparatus may be configured to allow to select the relationship between the infusion rate at the time of injection of a dialysis solution and the infusion rate of the dialysis solution at the time of discharge.

In addition, although not specifically referred to in the first embodiment, the apparatus may be configured to provide, as a selection auxiliary means for selection of an explanation mode ("short guide mode", "simplified guide mode", "normal guide", or "detailed guide mode") in accordance with the level of proficiency in operation, a means for storing, in a storage unit, the levels of the respective explanation modes and the numbers of times the touch panel has been operated at the respective levels to determine the level of proficiency in operation of a patient and automatically selecting an explanation mode optimal for the patient who uses the explanation mode.

Assume that a given patient frequently makes a specific operation mistake while operating in an explanation mode of an upper level. In this case, when the patient makes a predetermined number of operation mistakes or more (for example, three or four mistakes), the apparatus determines that the patient cannot operate only in the explanation mode of the current level, and automatically makes transition to the explanation mode of one level lower than the current mode to give an explanation of only an operation procedure associated with the operation.

In addition, the explanation modes to be prepared may include at least three modes, namely "simplified guide mode", "normal guide mode", and "detailed guide mode".

Third Embodiment

The first and second embodiments are configured to give explanations in accordance with the levels of proficiency in operation of patients. However, the present invention is not limited to this. For example, a doctor or the like needs to explain to a patient who is to use a peritoneal dialysis apparatus for the first time how to perform peritoneal dialysis by using the apparatus from the beginning. However, giving explanations while skipping explanations of some of the operation procedures will lead to a lack of sense of realism.

For this reason, this embodiment is configured to give a patient who is to use the peritoneal dialysis apparatus for the first time explanations according to operation procedures for actual medical treatment without actually performing medical treatment based on prescriptions. A peritoneal dialysis apparatus 100 of this embodiment is described below.

1. Description of Operation Procedure Explanation Function and Training Function The operation procedure explanation function of the peritoneal dialysis apparatus 100 according to this embodiment has features in a normal mode as an output mode based on the premise that a patient is to perform peritoneal dialysis upon mounting a cassette 130 in the apparatus and a training mode of performing only display of a display window without mounting the cassette 130.

The training mode is a mode effective when a doctor or the like explains to a patient about operation procedures for peritoneal dialysis or when operating the peritoneal dialysis apparatus without actually mounting the cassette 130 (that is, without using a dialysis solution).

In the following description, the peritoneal dialysis apparatus 100 is configured to prepare four explanation modes (a short guide mode, simplified guide mode, normal guide mode, and detailed guide mode) in accordance with the levels of proficiency in operation of patients, in consideration of different levels of proficiency in operation of patients, and subordinate the normal mode and training mode to the normal guide mode. However, the present invention is not limited to this. The number of explanation modes to be prepared need not be four. In addition, the destination to which the normal mode and the training mode are to be subordinated is not limited to the normal guide mode and may be another explanation mode.

(1) Description of Explanation Modes and Output Modes

Figure 10:
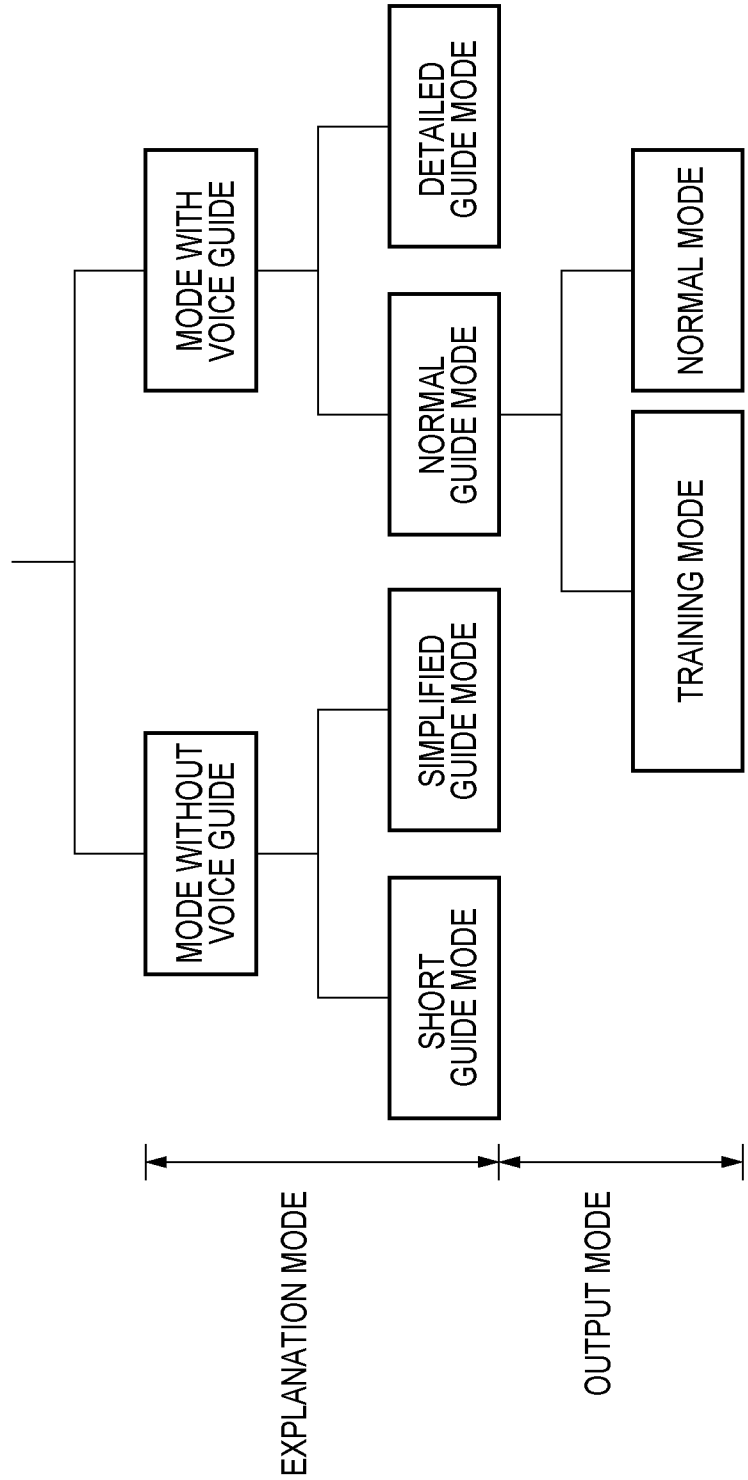
FIG. 10 is a view showing explanation modes and output modes in the display unit of the peritoneal dialysis apparatus 100.

FIG. 10 is a view showing the explanation modes of the operation procedure explanation function of the tomography apparatus 100 according to this embodiment. As shown in FIG. 10, this embodiment includes four modes, namely the short guide mode, simplified guide mode, normal guide mode, and detailed guide mode, as explanation modes, and two modes, namely the training mode and normal mode, as output modes.

Of these modes, the short guide mode, simplified guide mode, normal guide mode, and detailed guide mode constituting explanation modes have already been described, and hence a description of them is omitted.

The normal mode as an output mode is a mode based on the premise that peritoneal dialysis is performed upon mounting of the cassette 130. The training mode is a mode of displaying a display window and outputting a voice guide corresponding to the display of the display window without mounting the cassette 130. If a patient feels annoying, it is possible to inhibit a voice guide from being output (to turn the sound volume to zero).

In this mode arrangement, when a doctor or the like selects the normal guide mode from the four explanation modes displayed on a display unit 111-3 having the touch panel function upon pressing a start instruction unit 111-1, and further selects (presses) the training mode, it is possible to give the patient a detailed explanation of a method of performing peritoneal dialysis by using the peritoneal dialysis apparatus 100.

(2) Differences Between Normal Mode and Training Mode

Differences in display window transition between normal mode and the training mode of the normal guide mode is described next with reference to FIGS. 11A and 11B. When activating the operation procedure explanation function in the normal mode of the normal guide mode, the apparatus displays a display window 1111. Assume that after performing operation according to the operation procedure explained on the display window 1111, the patient inputs an instruction to proceed to the next display window. In this case, the current display window shifts to a display window 1112.

When the patient performs operation in accordance with an operation procedure explained on the display window 1112, to which transition has been made, to set the mounted cassette 130 in a predetermined state, the display window 1112 is automatically switched to a display window 1113.

Note that the predetermined state is a state in which a detection result on the state of the cassette 130 satisfies a predetermined condition, for example, a state in which a bubble sensor 112-3 does not notify the detection of bubbles for a predetermined period of time or a state in which the temperature detected by an outlet solution temperature sensor 462 falls within a predetermined temperature range.

When a patient activates the operation procedure explanation function in the training mode of the normal guide mode, the display window 1111 is displayed. When the patient inputs an instruction to proceed to the next display window upon performing operation in accordance with the operation procedure explained on the display window 1111, the current display window shifts to the display window 1112.

After the display window 1112 is displayed, display window transition automatically occurs in the order of display window 1112→display window 1113 regardless of whether the patient has performed operation in accordance with the operation procedure explained on the display window 1112 (that is, regardless of whether the mounted cassette 130 is set in the predetermined state).

As described above, the peritoneal dialysis apparatus 100 according to this embodiment can display the same display windows as those displayed when the cassette 130 is actually mounted, regardless of whether the cassette 130 is actually mounted. This allows a doctor or the like to give a patient or the like who is to use the peritoneal dialysis apparatus for the first time comprehensive explanations of operation procedures by using actual display windows.

2. Procedure for Window Transition Processing

Figure 11A:
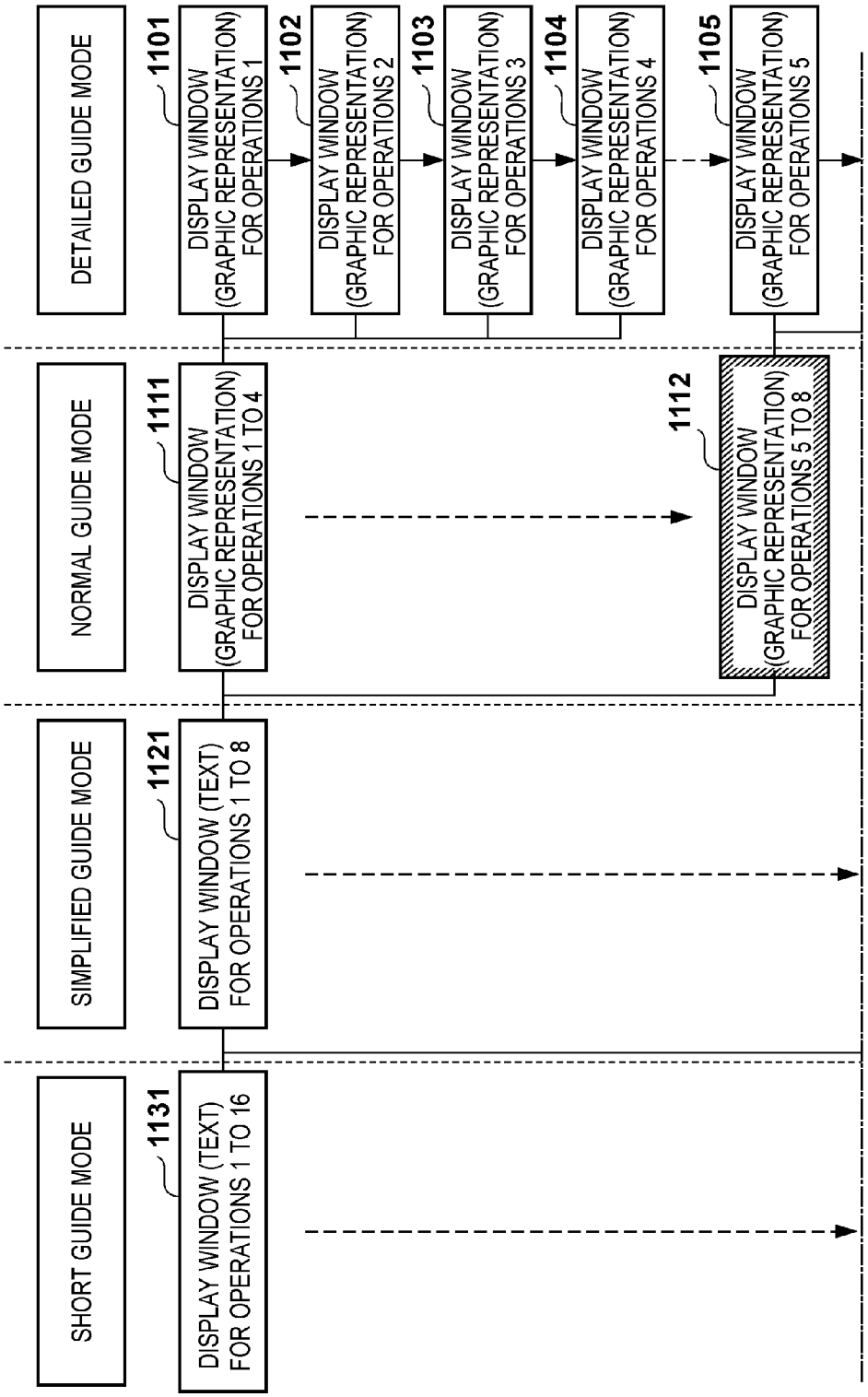

A procedure for display window transition processing in the operation procedure explanation function, which has been described with reference to specific examples using FIGS. 11A and 11B, is described again with reference to the flowchart shown in FIG. 12.

In step S1201, the apparatus determines whether the currently displayed display window is a display window which can be switched when it is detected that the mounted cassette is in the predetermined state.

If the apparatus determines in step S1201 that the currently displayed display window is a display window which can be switched when it is detected that the mounted cassette is in the predetermined state, the process advances to step S1202. In step S1202, the apparatus determines whether the selected output mode is the training mode.

If the apparatus determines in step S1202 that the output mode is the training mode, the process advances to step S1203 to switch the current display window to the next display window at the timing when a predetermined period of time has elapsed. If the apparatus determines that the output mode is not the training mode, the process advances to step S1204 to switch the current display window to the next display window at the timing when it is detected that the cassette 130 is in the predetermined state.

If the apparatus determines in step S1201 that the currently displayed display window is not a display window which can be switched when it is detected that the mounted cassette is in the predetermined state, the process advances to step S1205. In step S1205, the apparatus switches the current display window to the next or previous display window at the timing when the button "next" is pressed to issue an instruction to proceed to the next display window or the button "return" is pressed to issue an instruction to return to the previous display window.

As is obvious from the above description, the peritoneal dialysis apparatus 100 according to this embodiment can give a patient explanations according to actual operation procedures even when peritoneal dialysis is not actually performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-218496 filed on Sep. 29, 2010, and No. 2010-220406 filed on Sep. 30, 2010, which are hereby incorporated by reference herein in their entirety.

What is claimed is:

1. A peritoneal dialysis apparatus which is a home medical apparatus configured to display an operation procedure on a display unit, comprising:
   a selection unit configured to select one of a plurality of explanation modes having different contents of explanations associated with the operation procedure in accordance with levels of proficiency in the operation procedure;
   a storage unit configured to store a plurality of display windows displaying explanations associated with the operation procedure upon classifying the display windows to explanation modes corresponding to the levels of proficiency in the operation procedure in accordance with contents of the respective explanations, and storing display windows, of the plurality of display windows classified to the respective explanation modes, which are classified to explanation modes of adjacent levels when the explanation modes are hierarchically ranked in accordance with the levels of proficiency in the operation procedure, upon associating the display windows with each other in accordance with an operation purpose; and
   a display control unit configured to display display-windows classified to an explanation mode selected by said selection unit on the display unit in a predetermined order;
   wherein the plurality of explanation modes includes at least four explanation modes including:
   a detailed guide mode which is a detailed guide for an operator who uses the peritoneal dialysis apparatus for the first time, wherein in the detailed guide mode, a guide is performed to explain each operation procedure by using one window with a combination of voice and graphic representation including texts and pictures;
   a normal guide mode which is an explanation mode, wherein in the normal guide mode, a guide is performed to explain a plurality of operation procedures as one group by using one window with a combination of voice and graphic representation including texts and pictures;
   a simplified guide mode which is an explanation mode of further grouping a plurality of operation procedures, which are grouped in accordance with the purpose of operation in the normal guide mode, into one group, and explaining the grouped operation procedures by using one window with texts while reading the grouped operation procedures aloud; and
   a short guide mode which is an explanation mode of displaying further a plurality of operation procedures by using one window with texts while reading the operation procedures aloud, in comparison with the simplified guide mode.

2. The apparatus according to claim 1,
   wherein said display unit is a touch panel,
   wherein said storage unit further stores, as selection auxiliary information, levels of the respective explanation modes and the numbers of times the touch panel has been operated at the respective levels, and
   wherein said selection unit selects one explanation mode in accordance with a level of proficiency in the operation procedure based on the selection auxiliary information stored in said storage unit.

3. The apparatus according to claim 1, further comprising a determination unit configured to determine whether or not a predetermined number of operation mistakes or more while operating in an explanation mode is made,
   wherein if a predetermined number of specific operation mistakes or more is made, the apparatus determines that the operator cannot operate only in the explanation mode of the current level, and automatically makes transition to the explanation mode of one level lower than the current mode to give an explanation of only an operation procedure associated with the operation.

* * * * *